(12) United States Patent
Omenetto et al.

(10) Patent No.: US 9,761,789 B2
(45) Date of Patent: Sep. 12, 2017

(54) SILK-BASED PIEZOELECTRIC MATERIALS

(75) Inventors: Fiorenzo Omenetto, Lexington, MA (US); David Kaplan, Concord, MA (US); Tuna Yucel, Medford, MA (US)

(73) Assignee: Tufts University, Medford, MA (US)

( * ) Notice: Subject to any disclaimer, the term of this patent is extended or adjusted under 35 U.S.C. 154(b) by 1041 days.

(21) Appl. No.: 13/876,472

(22) PCT Filed: Sep. 27, 2011

(86) PCT No.: PCT/US2011/053551
§ 371 (c)(1),
(2), (4) Date: Nov. 22, 2013

(87) PCT Pub. No.: WO2012/047682
PCT Pub. Date: Apr. 12, 2012

(65) Prior Publication Data
US 2014/0145365 A1    May 29, 2014

Related U.S. Application Data

(60) Provisional application No. 61/386,592, filed on Sep. 27, 2010, provisional application No. 61/439,576, filed on Feb. 4, 2011.

(51) Int. Cl.
| | | |
|---|---|---|
| H01L 41/193 | (2006.01) |
| H01L 21/02 | (2006.01) |
| H01L 41/45 | (2013.01) |
| A61N 1/365 | (2006.01) |
| A61N 1/378 | (2006.01) |
| H01L 41/113 | (2006.01) |
| H02N 2/18 | (2006.01) |

(52) U.S. Cl.
CPC ............ H01L 41/193 (2013.01); H01L 21/02 (2013.01); H01L 41/45 (2013.01); A61N 1/36578 (2013.01); A61N 1/3785 (2013.01); H01L 41/1132 (2013.01); H02N 2/18 (2013.01)

(58) Field of Classification Search
CPC ....... H01L 41/193; H01L 21/02; H01L 41/45; H01L 41/1132; A61N 1/36578; A61N 1/3785; H02N 2/18
See application file for complete search history.

(56) References Cited

U.S. PATENT DOCUMENTS

| 5,245,012 A | 9/1993 | Lombari et al. |
| 6,902,932 B2 | 6/2005 | Altman et al. |
| (Continued) | | |

FOREIGN PATENT DOCUMENTS

| WO | WO-97/08315 A1 | 3/1997 |
| WO | WO-03/056297 A2 | 7/2003 |
| WO | WO-04/000915 A2 | 12/2003 |
| (Continued) | | |

OTHER PUBLICATIONS

Agarwal, N. et al., Effect of moisture absorption on the thermal properties of *Bombyx mori* silk fibroin films, Journal of Applied Polymer Science, 63(3):401-410 (1997).

(Continued)

*Primary Examiner* — Robert J Grun
(74) *Attorney, Agent, or Firm* — Choate, Hall & Stewart, LLP

(57) ABSTRACT

The invention relates to methods and compositions for preparing silk-based piezoelectric materials and methods for increasing piezoelectricity in silk matrices.

32 Claims, 16 Drawing Sheets

(56) References Cited

U.S. PATENT DOCUMENTS

| | | |
|---|---|---|
| 2003/0133247 A1 | 7/2003 | Ajioka |
| 2009/0202614 A1 | 8/2009 | Kaplan et al. |

FOREIGN PATENT DOCUMENTS

| | | |
|---|---|---|
| WO | WO-2004/062697 A2 | 7/2004 |
| WO | WO-2005/000483 A1 | 1/2005 |
| WO | WO-2005/012606 A2 | 2/2005 |
| WO | WO-2005/123114 A2 | 12/2005 |
| WO | WO-2006/042287 A2 | 4/2006 |
| WO | WO-2006/076711 A2 | 7/2006 |
| WO | WO-2007/016524 A2 | 2/2007 |
| WO | WO-2007/103442 A1 | 9/2007 |
| WO | WO-2008/106485 A2 | 9/2008 |
| WO | WO-2008/118133 A2 | 10/2008 |
| WO | WO-2008/127401 A2 | 10/2008 |
| WO | WO-2008/150861 A1 | 12/2008 |
| WO | WO-2010036992 A2 | 4/2010 |

OTHER PUBLICATIONS

Altman, G.H. et al., Silk-based biomaterials, Biomaterials, 24(3):401-416 (2003).
Asakura, T. et al., Conformation Characterization of *Bombyx mori* Silk Fibroin in the Solid State by High-Frequency C Cross Polarization—Magic Angle Spinning NMR, X-ray Diffraction, and Infrared Spectroscopy, Macromolecules, 18:1841-1845 (1985).
Bini, E. et al., Mapping domain structures in silks from insects and spiders related to protein assembly, Journal of Molecular Biology, 335(1):27-40 (2004).
Fukada, E. and Takashita, S., Piezoelectric Constant in Oriented β-form Polypeptides, Japanese Journal of Applied Physics, 10(6):722-726 (1971).
Fukada, Eiichi, Piezoelectric properties of biological polymers, Quarterly Reviews of Biophysics, 16(1):59-87 (1983).
Fukada, Eiichi, Piezoelectricity of natural biomaterials, Ferroelectrics, 60(1):285-296 (1984).
Fukada, Eiichi, Recent Developments of Polar Piezoelectric Polymers, IEEE Transactions on Dielectrics and Electrical Insulation, 13(5):1110-1119 (2006).
Go, Y. et al., Magnetic orientation of poly-γ-benzyl-L-glutamate, Biochim. Biphys, Acta, 175:454-456 (1969).
Harvey, E. Newton, The Luminescence of Adhesive Tape, Science, 89(2316):460-461 (1939).
Horan, R.L. et al., In vitro degradation of silk fibroin, Biomaterials, 26(17):3385-3393 (2005).
Hu, X et al., Determining beta-sheet crytallinity in bribrous proteins by thermal analysis and infrared spectroscopy. Macromolecules 39: 6161-6170 (2006).
Hu, X. et al., Dynamic protein-water relationships during β-sheet formation. Micromolecules 41: 3939-3948 (2008).
Hu, X. et al., Microphase Separation Controlled β-Sheet Crystallization Kinetics in Fibrous Proteins, Macromolecules, 42:2079-2087 (2009).
Inoue, S. et al., Silk fibroin of *Bombyx mori* is secreted, assembling a high molecular mass elementary unit consisting of H-chain, L-chain, and P25, with a 6:6:1 molar ratio, Journal of Biological Chemistry, 245(51):40517-40518 (2000).
Ishida, M. et al., Solvent- and Mechanical-Treatment-Induced Conformation Transition of Silk Fibroins Studied by High-Resolution Solid-State C NMR Spectroscopy, Macromolecules, 23:88-94 (1990).
Jin, H.J. and Kaplan, D.L., Mechanism of silk processing in insects and spiders, Nature, 424(6952):1057-1061 (2003).
Jin, H.J. et al., Biomaterial films of *Bombyx mori* silk fibroin with poly(ethylene oxide), Biomacromolecules, 5(3):711-717 (2004).
Jin, H.J. et al., Electrospinning *Bombyx mori* silk with poly(ethylene oxide), Biomacromolecules, 3(6):1233-1239 (2002).

Jung, Christiane, Insight into protein structure and protein-ligand recognition by Fourier transform infrared spectroscopy, Journal of Molecular Recognition, 13:325-351 (2000).
Kikuchi, Y. et al, Structure of the *Bombyx mori* fibroin light-chain-encoding gene: upstream sequence elements common to the light and heavy chain, Gene 110: 151-158 (1992).
Kim, D. et al., Structure of the Drawn and Annealed Silk Fibroin Films, Sen'i Gakkaisahi, 53(9):365-279 (1997).
Kim, H. et al., Bone Regeneration on Macroporous Aqueous-Derived Silk 3-D Scaffolds, Macromolecular Bioscience, 7:643-655 (2007).
Kratky, O. et al., An Unstable Lattice in Silk Fibroin, Nature, 165:319-320 (1950).
Leisk, G. et al., Electrogelation for Protein Adhesives, Advanced Materials, 22:711-715 (2010).
Levin, Michael, Large-scale biophysics: ion flows and regeneration, Trends in Cell Biology, 17(6):261-270 (2007).
Lotz, B. and Cesari, F., The chemical structure and the crystalline structures of *Bombyx mori* silk fibroin, Biochimie, 61:205-214 (1979).
Lucas, F. et al., The silk fibroins, Advances in Protein Chemistry, 13:107-242 (1958).
Marsh, R. et al., An Investigation of the Structure of Silk Fibroin, Biochimica et Biophysica Acta, 16:1-34 (1955).
Meinel, L. et al., Silk based biomaterials to heal critical sized femur defects, Bone, 39(4):922-931 (2006).
Nazarov, R. et al., Porous 3-D scaffolds from regenerated silk fibroin, Biomacromolecules, 5(3):718-726 (2004).
Omenetto, F.G. and Kaplan, D.L., New Opportunities for an Ancient Material, Science, 329:528-531 (2010).
Rockwood, D. et al., Ingrowth of human mesenchymal stem cells into porous silk particle reinforced silk composite scaffolds: An in vitro study, Acta Biomater, 7(1):144-151 (2011).
Shen, Y. et al., Microstructural Characterization of *Bombyx mori* Silk Fibers, Macromolecules, 31:8857-8864 (1998).
Takei, F. et al., Further Evidence for Importance of the Subunit Combination of Silk Fibroin in its Efficient secretion from the Posterior Silk Gland Cells, J Cell Biol. 105: 175-180 (1987).
Tanaka, K. et al., Determination of the site of disulfide linkage between heavy and light chains of silk fibroin produced by *Bombyx mori*, Biochim. Biophys. Acta 1432: 92-103 (1999).
Tanaka, K. et al., Immunological Identification of the Major Disulfide-Linked Light Component of Silk Fibroin, J. Biochem 114(1): 1-4 (1993).
Tretinnikov, O. and Tamada, Y., Influence of Casting Temperature on the Near-Surface Structure and Wettability of Cast Silk Fibroin Films, Langmuir, 17:7406-7413 (2001).
Valluzzi, R. et al., Trigonal Crystal Structure of *Bombyx mori* Silk Incorporating a Threefold Helical Chain Conformation Found at the Air-Water Interface, Macromolecules, 29:8606-8614 (1996).
Valluzzi, R., et al., Orientation of silk III at the air-water interface, Int. J. Biol. Macromol., 24(2-3): 237-242 (1999).
Wang, et al., Sonification-induced Gelation of Silk Fibroin for Cell Encapsulation, Biomaterials, 29(8):1054-1064 (2008).
Wang, X. et al., Silk Nanospheres and Microspheres from Silk/PVA Blend Films for Drug Delivery, Biomaterials, 31(6):1025-1035 (2010).
Wilson, D. et al., Conformational Transitions in Model Silk Peptides, Biophysical Journal, 78:2690-2701 (2000).
Yucel, T. et al., Non-equilibrium Silk Fibroin Adhesives, J. Struct. Biol., 170(2):406-412 (2010).
Yucel, T. et al., Vortex-Induced Injectable Silk Fibroin Hydrogels, Biophysical Journal, 97:2044-2050 (2009).
Zhou, C.Z. et al, Fine organization of *Bombyx mori* fibroin heavy chain gene, Nucleic Acids Research, 28(12):2413-2419 (2000).
International Preliminary Report on Patentability of PCT/US2011/053551, 7 pages (dated Apr. 2, 2013).
International Search Report of PCT/US2011/053551, 4 pages (dated Jun. 29, 2012).
Wang et al., Nanolayer Biomaterial Coatings of Silk Fibroin for Controlled Release, J Control Release, 121(3):190-199 (2007).
Written Opinion of PCT/US2011/053551, 5 pages (dated Jun. 29, 2012).

(56) References Cited

OTHER PUBLICATIONS

Ando, Y., Piezoelectric and Related properties of Hydrated Silk Fibroin, Reports on Progress in Polymer Physics in Japan, Gakujutsu Bunken Fukyukai, Tokyo, JP, xxiii: 775-778 (1980).
Extended European Search Report for EP 11831323, 4 pages (dated Nov. 20, 2014).
Fukada, E. On the piezoelectric effect of silk fibers, Journal of the Physical Society of Japan, Physical Society of Japan, Tokyo, JP, 11(12): 1301 (1956).
Jin, H-J. et al., Silkworm Protein: Its possibility as an actuator, Proceedings of Spie: Smart Structures and Materials 2006: Electroactive Polymer Actuators and Devices (EAPAD), 6168: 616821-1-616821-7 (2006).

Silk film

Heating block

SILK-BASED PIEZOELECTRIC MATERIALS

RELATED APPLICATIONS

This application is a 35 U.S.C. §371 National Stage of International Application No. PCT/US2011/053551, entitled "SILK-BASED PIEZOELECTRIC MATERIALS" filed Sep. 27, 2011, which claims the benefit of and priority to U.S. Provisional Applications 61/386,592, entitled "Piezoelectric Silk-Based Materials for Biomedical Applications," filed Sep. 27, 2010, and 61/439,576, entitled "Piezoelectric Silk-Based Materials for Biomedical Applications," filed Feb. 4, 2011, the entire contents of which are incorporated herein by reference

GOVERNMENT SUPPORT

This invention was made with government support under grants EB002520 awarded by the National Institutes of Health and FA9550-07-1-0079 awarded by the United States Air Force. The government has certain rights in the invention.

BACKGROUND OF THE INVENTION

Piezoelectricity is the ability of certain materials (e.g., crystals, certain ceramics, and biological matter such as bone, DNA and various proteins) to convert mechanical energy into electrical energy or vice versa. Piezoelectric materials can be useful in numerous areas of application such as generating high voltage and/or power sources, sensors, or actuators, etc.

Conventional piezoelectric materials such as certain ceramics or synthetic polymers such as polyvinylidene fluoride may not be suitable for biomedical and biotechnological application due to lack of biocompatibility and biodegradability.

Silk fibroins of natural silkworm fibers have shown some shear piezoelectricity. See Ando et al., Reports on Progress in Polymer Physics in Japan 23, 775-8 (1980); Fukada, J. Phys. Soc. Jpn. 11, 1301 (1956); Harvey, Science 89, 460-1 (1939). Early research suggests that a reddish luminescence formed by shaking of silk fragments may be attributed to their piezoelectricity. See Harvey, Science 89, 460-1 (1939). However, this study was to focus on the natural silk fiber, rather than the regenerated silk matrix. Moreover, there has not been any insight into the mechanisms and structural changes that may be associated with the phenomena observed with silk materials. More importantly, no further studies have been provided to control silk piezoelectricity at a desired level for various applications. Hence there is still a need in the art to develop a piezoelectric material that can be biocompatible and controllably biodegradable for applications such as biomedical materials, tissue engineering and medical devices.

SUMMARY OF THE INVENTION

Among other things, the present invention encompasses the recognition that silk materials can exhibit oscillatory behavior via piezoelectricity, much like quartz. When mechanical stress is applied, silk is capable of generating electric charge, which may then be captured. This property, coupled with the biocompatible nature of silk, is useful in a number of applications, including implantable sensors and energy-scavenging tools that can power low-powered devices in vivo. Among other biopolymers, silk is particularly suited for providing stable and robust oscillations when exhibiting piezoelectricity, based in part on its structural rigidity. When piezoelectric silk that can oscillate are certain frequencies is structurally perturbed (e.g., being deformed), such structural alteration can be detected by known methods, providing a basis for a sensing means. In addition, mechanical vibration of silk-based piezoelectric materials provides a means for capturing and storing energy for other purposes (e.g., energy scavenging). The present invention also includes the appreciation that the efficiency of energy conversion may be increased by enhanced alignment of silk fibroin polymers.

One aspect of the invention relates to a process for producing a piezoelectric material from silk. The process comprises the steps of providing a silk matrix, e.g., a silk film; heating at least a portion of the silk matrix at a temperature of no less than glass transition temperature of the silk matrix; and elongating the silk matrix. In certain embodiments, the heating and elongation steps are performed simultaneously. In some embodiments, the portion of the silk matrix is locally heated by moving a heating element along the length of the silk matrix, e.g., at a rate of about 0.5 mm/min to about 20 mm/min. In some embodiments, the silk film is elongated to a final length, where the ratio of the final length to the initial length of the silk film is at least about 2.0. In some embodiments, the silk film is elongated at a rate of about 0.5 mm/min to about 20 mm/min. In one embodiment, the silk film is elongated at a rate of about 10 mm/min. In one embodiment, the elongation step increases the amount of silk II crystals in the silk matrix and increases the degree of uniaxial alignment of the silk II crystals.

Another aspect of the invention relates to a process for increasing piezoelectricity in a silk matrix. The process comprises the steps of providing a silk matrix that contains a substantial amount of amorphous silk or is in a substantially isotropic silk I conformation; heating at least a portion of the silk matrix at a temperature of no less than glass transition temperature of the silk matrix; and elongating the silk matrix. In certain embodiments, the heating and drawing steps are performed simultaneously. In some embodiments, the portion of the silk matrix is locally heated by moving a heating element along the length of the silk matrix, e.g., at a rate of about 0.5 mm/min to about 20 mm/min. In some embodiments, the silk matrix is elongated to a final length, where the ratio of the final length to the initial length of the silk matrix is at least about 2.0. In some embodiments, the silk film is elongated at a rate of about 0.5 mm/min to about 20 mm/min. In one embodiment, the silk film is elongated at a rate of about 10 mm/min. In one embodiment, the elongation step increases the amount of silk II crystals in the silk matrix and increases the degree of uniaxial alignment of the silk II crystals.

A further aspect of the invention is directed to a process of increasing piezoelectricity in a silk matrix, e.g., at an ambient temperature. The process includes providing a silk matrix, contacting at least a portion of the provided silk matrix with an aqueous solvent, e.g., water, and elongating the silk matrix, e.g., the hydrated silk matrix, at an ambient temperature. In some embodiments, the silk matrix is elongated to a final length, where the ratio of the final length to the initial length of the silk matrix is at least about 2.0. In some embodiments, the silk film is elongated at a rate of about 0.5 mm/min to about 50 mm/min. In one embodiment, the silk matrix is a silk film.

Yet a further aspect of the invention relates to a piezoelectric material produced by the processes of the invention, and its applications thereof, for example, in a sensor or in a cardiac assistance device, e.g., a pacemaker.

BRIEF DESCRIPTION OF THE DRAWING

FIG. 2A shows the amide I band of silk films elongated at different elongation ratios, e.g., processed by zone drawing (elongation ratio $\lambda$=1.0, 1.5, 2.0 and 2.7 for spectra labeled from 1 to 4, respectively), and post zone-drawing annealing at 200° C. for one hour (elongation ratio $\lambda$=2.0, spectra 5). RC: random coil. FIG. 2B shows the amide I band and amide II band of silk films processed by different elongation methods (solid line: water immersion drawing; dashed line: zone drawing) at the same elongation ratio $\lambda$=2.0.

FIG. 8A shows the results of temperature/frequency sweeps of the storage modulus (E') from (0.1-79 Hz frequency, 0.02% strain). FIG. 8B shows the results of time evolution of frequency sweeps of E' during a 200° C. anneal.

DETAILED DESCRIPTION OF CERTAIN EMBODIMENTS

Figure 1A:
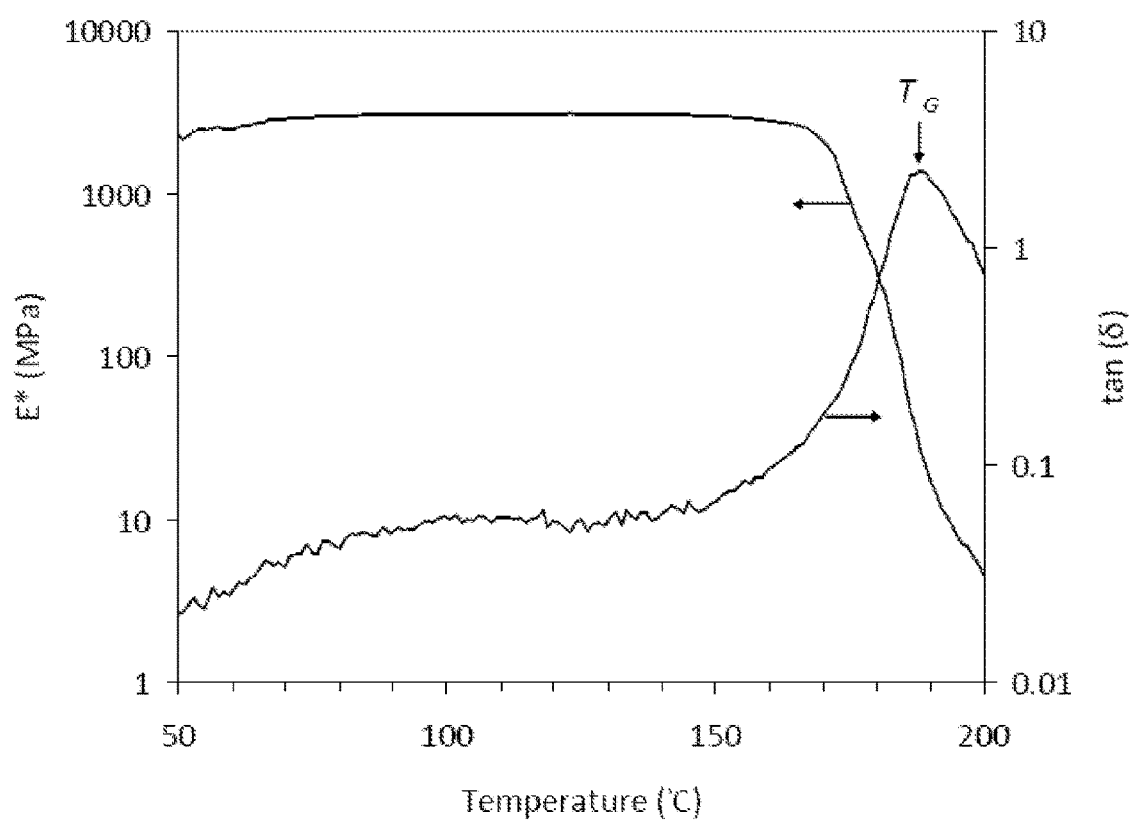
FIG. 1A shows the test results of the complex elastic modulus, E*, and the loss tangent, tan (δ), collected from a silk fibroin film, by using a dynamic mechanical analyzer (DMA) at the temperature sweep mode ($T_G \approx 190°$ C.).

The present disclosure relates to methods for preparing piezoelectric silk materials, methods for increasing piezoelectricity in silk matrices, and compositions resulted therefrom. Piezoelectricity can be the ability of certain crystalline materials that lack a center of symmetry to convert mechanical energy into electrical energy or vice versa. Piezoelectric elements are used to construct transducers for a vast number of different applications. Piezoelectric materials generate an electrical charge in response to mechanical movement, or vice versa, e.g., producing mechanical movement in response to electrical input. The basic theory behind piezoelectricity is based on the electrical dipole. At the molecular level, the structure of a piezoelectric material is typically an ionic bonded crystal. At rest, the dipoles formed by the positive and negative ions cancel each other due to the symmetry of the crystal structure, and an electric field is not observed. When stressed, the crystal deforms, symmetry is lost, and a net dipole moment is created. This dipole moment forms an electric field across the crystal.

Some polymer crystals also lack a symmetry center and therefore exhibit intrinsic piezoelectricity. See Hayakawa & Wada, *Advances in Polymer Science*, Vol. 11, Springer, New York, 1973, 1-56. Some uniaxially oriented, polycrystalline, biopolymeric materials show intrinsic shear piezoelectricity, i.e., an electrical polarization in response to shear deformation, in a direction perpendicular to the shear field. See Fukada, Q. Rev. Biophys. 16, 59-87 (1983).

One aspect of the present disclosure relates to piezoelectric silk materials, such as silk films. Piezoelectric silk material may exhibit oscillatory behavior. According to the invention, piezoelectric silk film may exhibit oscillatory behavior in response to perturbations. Exemplary perturbations may include applied voltage, applied power, mechanical stress (e.g., stresses resulting in physical deformation of the silk film), sound, any other force that may act upon the silk film, or any combination thereof. Perturbations may include any force that evokes a response from a piezoelectric substance.

In some embodiments, in response to voltage and/or power, a piezoelectric silk film may physically deform. In some embodiments, in response to mechanical stress, a piezoelectric silk film may produce charge, current, and/or voltage. In some embodiments, in response to sound waves, a piezoelectric silk film may produce charge, current, and/or voltage. The magnitude of the physical deformation, produced charge, produced current, and/or produced voltage of a piezoelectric silk film may be related to the magnitude of the perturbation (e.g., linearly related, proportional).

In some embodiments, piezoelectric silk film may exhibit oscillatory behavior at one or more resonant frequencies. In some embodiments, piezoelectric silk film may exhibit oscillatory behavior at frequencies between about 1 and about 999 kHz. In some embodiments, piezoelectric silk film may exhibit oscillatory behavior at frequencies between about 1 and about 999 MHz. In some embodiments, piezoelectric silk film may exhibit oscillatory behavior at frequencies between about 1 kHz and about 500 MHz. In some embodiments, piezoelectric silk films may exhibit oscillatory behavior at about 32 kHz or about 33 kHz. In some embodiments, piezoelectric silk films may exhibit oscillatory behavior at about 32,768 Hz. In some embodiments, piezoelectric silk films may exhibit oscillatory behavior between about 10 kHz and about 100 kHz. In some embodiments, piezoelectric silk films may exhibit oscillatory behavior at comparable frequencies as silicon dioxide (e.g., quartz).

In some embodiments, a piezoelectric silk matrix such as silk film may have a crystal or substantially crystal structure. The crystal structure may belong to the same crystal systems (e.g., classes of point groups) as quartz. In some embodiments, the crystal structure of a piezoelectric silk matrix may belong to the trigonal crystal system. In some embodiments, the crystal structure of a piezoelectric silk film may belong to the tetragonal crystal system.

In some embodiments, the crystal structure of a piezoelectric silk film may be symmetrical. For example, the crystal structure of a piezoelectric silk film may have at least one threefold axis of rotation or at least one fourfold axis of rotation. In some embodiments, components of the piezoelectric silk film may be arranged as six-sided prisms, each prism terminating with six-sided pyramids at each end.

In some embodiments, a piezoelectric silk film may have a Mohs hardness value of about 7. In some embodiments, a piezoelectric silk film may have a Vickers indentation hardness of about 1181 kg/mm2, about 1103 kg/mm2, or about 1260 kg/mm2. In some embodiments, a piezoelectric silk film may have a Rosival grinding hardness value of about 100.

In some embodiments, a piezoelectric silk film may have a Young's modulus of about 100 gigapascals (GPa). In some embodiments, a piezoelectric silk film may have a Young's modulus between about 80 and about 120 gigapascals (GPa). In some embodiments, a piezoelectric silk film may have a Young's modulus between about 12,000,000 lbf/in$^2$ (psi) and about 17,500,000 lbf/in$^2$ (psi).

In some embodiments, a piezoelectric silk film may have a Q factor of about 90 to about 115. In some embodiments, a piezoelectric silk film may have a Q factor of about 104, 105, 106, or 107.

One aspect of the invention relates to a process for producing a piezoelectric material from silk. The process comprises the steps of providing a silk matrix, e.g., a silk film; heating at least a portion of the silk matrix at a temperature of no less than glass transition temperature; and elongating the silk matrix. In certain embodiments, the heating and elongation steps are performed simultaneously. In some embodiments, the portion of the silk matrix is locally heated by moving a heating element along the length of the silk matrix, e.g., at a rate of about 0.5 mm/min to about 20 mm/min. In some embodiments, the silk film is elongated to a final length, where the ratio of the final length to the initial length of the silk film is at least about 2.0. In some embodiments, the silk film is elongated at a rate of about 0.5 mm/min to about 20 mm/min. In one embodiment, the elongation step increases the amount of silk II crystals in the silk matrix and increases the degree of uniaxial alignment of the silk II crystals.

Another aspect of the invention relates to a process for increasing piezoelectricity in a silk matrix. The process comprises the steps of providing a silk matrix that contains a substantial amount of amorphous silk or is in a substantially isotropic silk I conformation; heating at least a portion of the silk matrix at a temperature of no less than glass transition temperature of the silk matrix; and elongating the silk matrix. In one embodiment, the heating and elongation steps are performed simultaneously. In some embodiments, the portion of the silk matrix is locally heated by moving a heating element along the length of the silk matrix, e.g., at a rate of about 0.5 mm/min to about 20 mm/min. In some embodiments, the silk matrix is elongated to a final length, where the ratio of the final length to the initial length of the silk matrix is at least about 2.0. In some embodiments, the silk film is elongated at a rate of about 0.5 mm/min to about 20 mm/min. In one embodiment, the elongation step increases the amount of silk II crystals in the silk matrix and increases the degree of uniaxial alignment of the silk II crystals.

As used herein, the term "substantial amount" or "substantially", in reference to content of amorphous silk or isotropic silk I conformation in a silk matrix, means that the silk matrix contains at least about 20%, at least about 30%, at least about 40%, at least about 50%, at least about 60%, at least about 70%, at least about 80%, at least about 90%, at least about 95%, about 96%, about 97%, about 98%, about 99%, or 100% of amorphous silk or isotropic silk I conformation.

Embodiments of this invention nevertheless demonstrate that silk piezoelectricity can be controlled by varying parameters for processing silk materials, including but not limited to, elongation method, elongation ratio, and post-elongation treatment. To produce a strong piezoelectric effect in silk matrices, coherent increases of both the silk II, β-sheet crystallinity and the crystalline orientation are desirable.

In embodiments of the invention, a silk matrix, e.g., a silk film, provided for producing a silk-based piezoelectric material and/or increasing piezoelectricity thereof are generated from silk fibroin solution. Silk fibroin is a high molecular weight block copolymer consisting of a heavy chain (≈370 kDa) and a light chain (≈26 kDa). These two chains having different amphiphilicity are linked together by a single disulfide bond. See Inoue et al., J. Biol. Chem. 275, 40517 (2000). The heavy chain predominantly consists of alternating hydrophobic, repetitive oligopeptides that are separated by smaller charged and amorphous sequences. The hydrophobic domain is rich in alanine and glycine amino acids, while the hydrophilic spacers render the heavy chain a polyelectrolyte nature. The sequence of the light chain is less repetitive and contains a high concentration of glutamic and aspartic acid residues. In Nature, the crystalline regions in semicrystalline fibroin fibers assume a silk II form, a pleated, antiparallel β-sheet secondary structure with a monoclinic unit cell. See Lotz & Cesari, Biochimie 61, 205-14 (1979); Marsh et al., Biochimica Et Biophysica Acta 16, 1-34 (1955). Silk fibroin is known to display crystalline polymorphism. One such polymorph, silk I (see Kratky et al., Nature 165, 319-20 (1950)) is considered to be a predominantly helical, less extended conformation of silk chains, as compared with silk II. With the application of shear, the metastable silk I structure typically transitions into silk II. Silk III, on the other hand, is a three-fold, helical conformation found in thin films at the air-water interface with an overall trigonal unit cell. See Valluzzi et al., Macromolecules 29, 8606-14 (1996).

As used herein, the term "silk fibroin" includes silkworm fibroin and insect or spider silk protein. See e.g., Lucas et al., Adv. Protein Chem. 13, 107 (1958). Any type of silk fibroin may be used. Silk fibroin produced by silkworms, such as *Bombyx mori*, is the most common and represents an earth-friendly, renewable resource. For instance, silk fibroin may be attained by extracting sericin from the cocoons of *B. mori*. Organic silkworm cocoons are also commercially available. There are many different silks, however, including spider silk (e.g., obtained from *Nephila clavipes*), transgenic silks, genetically engineered silks, such as silks from bacteria, yeast, mammalian cells, transgenic animals, or transgenic plants (see, e.g., WO 97/08315; U.S. Pat. No. 5,245, 012), and variants thereof, that may be used.

As stated above, silk for use in accordance with the present invention may be produced by any such organism, or may be prepared through an artificial process, for example, involving genetic engineering of cells or organisms to produce a silk protein and/or chemical synthesis. In some embodiments of the present invention, silk is produced by the silkworm, *Bombyx mori*.

As is known in the art, silks are modular in design, with large internal repeats flanked by shorter (~100 amino acid) terminal domains (N and C termini). Silks have high molecular weight (200 to 350 kDa or higher) with transcripts of 10,000 base pairs and higher and >3000 amino acids (reviewed in Omenatto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules.

Table 1, below, provides an exemplary list of silk-producing species and silk proteins:

TABLE 1

An exemplary list of silk-producing species and silk proteins (adopted from Bini et al. (2003), J. Mol. Biol. 335(1): 27-40).

| Accession | Species | Producing gland | Protein |
|---|---|---|---|
| A. Silkworms | | | |
| AAN28165 | Antheraea mylitta | Salivary | Fibroin |
| AAC32606 | Antheraea pernyi | Salivary | Fibroin |
| AAK83145 | Antheraea yamamai | Salivary | Fibroin |
| AAG10393 | Galleria mellonella | Salivary | Heavy chain fibroin (N-terminal) |
| AAG10394 | Galleria mellonella | Salivary | Heavy chain fibroin (C-terminal) |
| P05790 | Bombyx mori | Salivary | Fibroin heavy chain precursor, Fib-H, H-fibroin |
| CAA27612 | Bombyx mandarina | Salivary | Fibroin |
| Q26427 | Galleria mellonella | Salivary | Fibroin light chain precursor, Fib-L, L-fibroin, PG-1 |
| P21828 | Bombyx mori | Salivary | Fibroin light chain precursor, Fib-L, L-fibroin |
| B. Spiders | | | |
| P19837 | Nephila clavipes | Major ampullate | Spidroin 1, dragline silk fibroin 1 |
| P46804 | Nephila clavipes | Major ampullate | Spidroin 2, dragline silk fibroin 2 |
| AAK30609 | Nephila senegalensis | Major ampullate | Spidroin 2 |
| AAK30601 | Gasteracantha mammosa | Major ampullate | Spidroin 2 |
| AAK30592 | Argiope aurantia | Major ampullate | Spidroin 2 |
| AAC47011 | Araneus diadematus | Major ampullate | Fibroin-4, ADF-4 |
| AAK30604 | Latrodectus geometricus | Major ampullate | Spidroin 2 |
| AAC04503 | Araneus bicentenarius | Major ampullate | Spidroin 2 |
| AAK30615 | Tetragnatha versicolor | Major ampullate | Spidroin 1 |
| AAN85280 | Araneus ventricosus | Major ampullate | Dragline silk protein-1 |
| AAN85281 | Araneus ventricosus | Major ampullate | Dragline silk protein-2 |
| AAC14589 | Nephila clavipes | Minor ampullate | MiSp1 silk protein |
| AAK30598 | Dolomedes tenebrosus | Ampullate | Fibroin 1 |
| AAK30599 | Dolomedes tenebrosus | Ampullate | Fibroin 2 |
| AAK30600 | Euagrus chisoseus | Combined | Fibroin 1 |
| AAK30610 | Plectreurys tristis | Larger ampule-shaped | Fibroin 1 |
| AAK30611 | Plectreurys tristis | Larger ampule-shaped | Fibroin 2 |
| AAK30612 | Plectreurys tristis | Larger ampule-shaped | Fibroin 3 |
| AAK30613 | Plectreurys tristis | Larger ampule-shaped | Fibroin 4 |
| AAK30593 | Argiope trifasciata | Flagelliform | Silk protein |
| AAF36091 | Nephila madagascariensis | Flagelliform | Fibroin, silk protein (N-terminal) |
| AAF36092 | Nephila madagascariensis | Flagelliform | Silk protein (C-terminal) |
| AAC38846 | Nephila clavipes | Flagelliform | Fibroin, silk protein (N-terminal) |
| AAC38847 | Nephila clavipes | Flagelliform | Silk protein (C-terminal) |

Fibroin is a type of structural protein produced by certain spider and insect species that produce silk. Cocoon silk produced by the silkworm, *Bombyx mori*, is of particular interest because it offers low-cost, bulk-scale production suitable for a number of commercial applications, such as textile.

As mentioned, silkworm cocoon silk contains two structural proteins, the fibroin heavy chain (~350-370 kDa) and the fibroin light chain (~25-26 kDa), which are associated with a family of non-structural proteins termed sericin, which glue the fibroin brins together in forming the cocoon. The heavy and light chains of fibroin are linked by a disulfide bond at the C-terminus of the two subunits (Takei, F., Kikuchi, Y., Kikuchi, A., Mizuno, S, and Shimura, K. (1987) J. Cell Biol., 105, 175-180; Tanaka, K., Mori, K. and Mizuno, S. (1993) J. Biochem. (Tokyo), 114, 1-4; Tanaka, K., Kajiyama, N., Ishikura, K., Waga, S., Kikuchi, A., Ohtomo, K., Takagi, T. and Mizuno, S. (1999) Biochim. Biophys. Acta, 1432, 92-103; Y Kikuchi, K Mori, S Suzuki, K Yamaguchi and S Mizuno, Structure of the *Bombyx mori* fibroin light-chain-encoding gene: upstream sequence elements common to the light and heavy chain, Gene 110 (1992), pp. 151-158). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., Adv. Protein Chem., 13: 107-242 (1958)). In some embodiments, silk fibroin is obtained from a solution containing a dissolved silkworm silk or spider silk. For example, in some embodiments, silkworm silk fibroins are obtained, from the cocoon of *Bombyx mori*. In some embodiments, spider silk fibroins are obtained, for example, from *Nephila clavipes*. In the alternative, in some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

Thus, in some embodiments, a silk solution is used to fabricate compositions of the present invention contain fibroin proteins, essentially free of sericins. In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds.

Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" hydrophobic blocks are typically separated by segments of amino acids with bulky side-groups (e.g., hydrophilic spacers).

In some embodiments, core repeat sequences of the hydrophobic blocks of fibroin are represented by the following amino acid sequences and/or formulae: $(GAGAGS)_{5-15}$ (SEQ ID NO: 1); $(GX)_{5-15}$ (X=V, I, A) (SEQ ID NO: 2); GAAS (SEQ ID NO: 3); $(S_{1-2}A_{11-3})$ (SEQ ID NO: 4); $GX_{1-4}$ GGX (SEQ ID NO: 5); GGGX (X=A, S, Y, R, D V, W, R, D) (SEQ ID NO: 6); $(S_{1-2}A_{1-4})_{1-2}$ (SEQ ID NO: 7); GLGGLG (SEQ ID NO: 8); GXGGXG (X=L, I, V, P) (SEQ ID NO: 9); GPX (X=L, Y, I); $(GP(GGX)_{1-4} Y)n$ (X=Y, V, S, A) (SEQ ID NO: 10); GRGGAn (SEQ ID NO: 11); GGXn (X=A, T, V, S); $GAG(A)_{6-7}GGA$ (SEQ ID NO: 12); and GGX GX GXX (X=Q, Y, L, A, S, R) (SEQ ID NO: 13).

In some embodiments, a fibroin peptide contains multiple hydrophobic blocks, e.g., 3, 4, 5, 6, 7, 8, 9, 10, 11, 12, 13, 14, 15, 16, 17, 18, 19 and 20 hydrophobic blocks within the peptide. In some embodiments, a fibroin peptide contains between 4-17 hydrophobic blocks.

In some embodiments of the invention, a fibroin peptide comprises at least one hydrophilic spacer sequence ("hydrophilic block") that is about 4-50 amino acids in length. Non-limiting examples of the hydrophilic spacer sequences include: TGSSGFGPYVNGGYSG (SEQ ID NO: 14); YEYAWSSE (SEQ ID NO: 15); SDFGTGS (SEQ ID NO: 16); RRAGYDR (SEQ ID NO: 17); EVIVIDDR (SEQ ID NO: 18); TTIIEDLDITIDGADGPI (SEQ ID NO: 19) and TISEELTI (SEQ ID NO: 20).

In certain embodiments, a fibroin peptide contains a hydrophilic spacer sequence that is a derivative of any one of the representative spacer sequences listed above. Such derivatives are at least 75%, at least 80%, at least 85%, at least 90%, or at least 95% identical to any one of the hydrophilic spacer sequences.

In some embodiments, a fibroin peptide suitable for the present invention contains no spacer.

As noted, silks are fibrous proteins and are characterized by modular units linked together to form high molecular weight, highly repetitive proteins. These modular units or domains, each with specific amino acid sequences and chemistries, are thought to provide specific functions. For example, sequence motifs such as poly-alanine (polyA) and poly-alanine-glycine (poly-AG) are inclined to be beta-sheet-forming; GXX motifs contribute to 31-helix formation; GXG motifs provide stiffness; and, GPGXX (SEQ ID NO: 22) contributes to beta-spiral formation. These are examples of key components in various silk structures whose positioning and arrangement are intimately tied with the end material properties of silk-based materials (reviewed in Omenetto and Kaplan (2010) Science 329: 528-531).

It has been observed that the beta-sheets of fibroin proteins stack to form crystals, whereas the other segments form amorphous domains. It is the interplay between the hard crystalline segments, and the strained elastic semi amorphous regions, that gives silk its extraordinary properties. Non-limiting examples of repeat sequences and spacer sequences from various silk-producing species are provided in Table 2 below.

TABLE 2

Hydrophobic and hydrophilic components of fibroin sequences (adopted from Bini et al. (2003), J. Mol. Biol. 335(1): 27-40).

| Species | Hydrophilic blocks | | | Hydrophobic blocks | | |
|---|---|---|---|---|---|---|
| | N-term aa | C-term aa | Hydrophilic spacer (aa) & representative sequence | Range, aa | # of Blocks | Core repeat sequences |
| A. Lepidoptera (Heavy chain fibroin) | | | | | | |
| Bombyx mori | 151 | 50 | 32-33, TGSSGFGPYVNGGYSG, (SEQ ID NO: 14) | 159-607 | 12 | $(GAGAGS)_{5-15}$, (SEQ ID NO: 1); $(GX)_{5-15}$ (X = V, I, A), (SEQ ID NO: 2); GAAS (SEQ ID NO: 3) |
| Bombyx mandarina | 151 | | YEYAWSSE, (SEQ ID NO: 15) | | | |
| Antheraea mylitta | 86 | | SDFGTGS, (SEQ ID NO: 16) | | | |

TABLE 2-continued

Hydrophobic and hydrophilic components of fibroin sequences
(adopted from Bini et al. (2003), J. Mol. Biol. 335(1): 27-40).

| Species | Hydrophilic blocks | | | Hydrophobic blocks | | |
|---|---|---|---|---|---|---|
| | N-term aa | C-term aa | Hydrophilic spacer (aa) & representative sequence | Range, aa | # of Blocks | Core repeat sequences |
| Antheraea pernyi | 87 | 32 | | | | |
| Antheraea yamamai | 87 | 32 | 7, RRAGYDR, (SEQ ID NO: 17) | 140-340 | 16 | $(S_{1-2}A_{11-13})$, (SEQ ID NO: 4); $GX_{1-4}$ GGX, (SEQ ID NO: 5); GGGX (X = A, S, Y, R, D V, W, R, D), (SEQ ID NO: 6) |
| Galleria mellonella | 189 | 60 | 6-8, EVIVIDDR, (SEQ ID NO: 18) | 75-99 | 13 | $(S_{1-2}A_{1-4})_{1-2}$, (SEQ ID NO: 7); GLGGLG, (SEQ ID NO: 8); GXGGXG (X = L, I, V, P), (SEQ ID NO: 9); GPX (X = L, Y, I) |
| B. Arachnida | | | | | | |
| Nephila clavipes | 115 | 89 | | | | |
| Nephila madascariensis | 115 | 89 | 26, TTIIEDLDITIDG ADGPI, (SEQ ID NO: 19) | 260-380 | 5 | (GP(GGX)1-4 Y)n (X = Y, V, S, A), (SEQ ID NO: 10) |
| Argiope trifasciata | | 113 | | | | GRGGAn, (SEQ ID NO: 11) GGXn (X = A, T, V, S) |
| Major ampullata | | | TISEELTI, (SEQ ID NO: 20) | | | |
| Nephila clavipes | | 97 | No spacer | 19-46 | | $GAG(A)_{6-7}GGA$, (SEQ ID NO: 12); GGX GX GXX(X = Q, Y, L, A, S, R), (SEQ ID NO: 13) |
| Gasteracantha mammosa | | 89 | No spacer | | | |
| Argiope aurantia | | 82 | No spacer | | | |
| Nephila senegalensis | | 82 | No spacer | | | |
| Latrodectus geometricus | | 88 | No spacer | | | |
| Araneus diadematus | | 94 | No spacer | | | |

The particular silk materials explicitly exemplified herein were typically prepared from material spun by silkworm, *B. Mori*. Typically, cocoons are boiled for ~30 min in an aqueous solution of 0.02M $Na_2CO_3$, then rinsed thoroughly with water to extract the glue-like sericin proteins. The extracted silk is then dissolved in LiBr (such as 9.3 M) solution at room temperature, yielding a 20% (wt.) solution. The resulting silk fibroin solution can then be further processed for a variety of applications as described elsewhere herein. Those of ordinary skill in the art understand other sources available and may well be appropriate, such as those exemplified in the Table above.

The complete sequence of the *Bombyx mori* fibroin gene has been determined (C.-Z Zhou, F Confalonieri, N Medina, Y Zivanovic, C Esnault and T Yang et al., Fine organization of *Bombyx mori* fibroin heavy chain gene, Nucl. Acids Res. 28 (2000), pp. 2413-2419). The fibroin coding sequence presents a spectacular organization, with a highly repetitive and G-rich (~45%) core flanked by non-repetitive 5' and 3' ends. This repetitive core is composed of alternate arrays of 12 repetitive and 11 amorphous domains. The sequences of the amorphous domains are evolutionarily conserved and the repetitive domains differ from each other in length by a variety of tandem repeats of subdomains of ~208 bp.

The silkworm fibroin protein consists of layers of antiparallel beta sheets whose primary structure mainly consists of the recurrent amino acid sequence (Gly-Ser-Gly-Ala-Gly-Ala)n (SEQ ID NO: 21). The beta-sheet configuration of fibroin is largely responsible for the tensile strength of the material due to hydrogen bonds formed in these regions. In addition to being stronger than Kevlar, fibroin is known to be highly elastic. Historically, these attributes have made it a material with applications in several areas, including textile manufacture.

Fibroin is known to arrange itself in three structures at the macromolecular level, termed silk I, silk II, and silk III, the first two being the primary structures observed in nature. The silk II structure generally refers to the beta-sheet conformation of fibroin. Silk I, which is the other main crystal structure of silk fibroin, is a hydrated structure and is considered to be a necessary intermediate for the preorganization or prealignment of silk fibroin molecules. In the nature, silk I structure is transformed into silk II structure after spinning process. For example, silk I is the natural form of fibroin, as emitted from the *Bombyx mori* silk glands. Silk II refers to the arrangement of fibroin molecules in spun silk, which has greater strength and is often used commercially in various applications. As noted above, the amino-acid sequence of the β-sheet forming crystalline region of fibroin is dominated by the hydrophobic sequence. Silk fibre formation involves shear and elongational stress acting on the fibroin solution (up to 30% wt/vol.) in the gland, causing fibroin in solution to crystallize. The process involves a lyotropic liquid crystal phase, which is transformed from a gel to a sol state during spinning—that is, a liquid crystal spinning process. Elongational flow orients the fibroin chains, and the liquid is converted into filaments.

Silk III is a newly discovered structure of fibroin (Valluzzi, Regina; Gido, Samuel P.; Muller, Wayne; Kaplan, David L. (1999). "Orientation of silk III at the air-water interface." International Journal of Biological Macromolecules 24: 237-242). Silk III is formed principally in solutions of fibroin at an interface (i.e. air-water interface, water-oil interface, etc.).

Silk can assemble, and in fact can self-assemble, into crystalline structures. Silk fibroin can be fabricated into desired shapes and conformations, such as silk hydrogels (WO2005/012606; PCT/US08/65076), ultrathin films (WO2007/016524), thick films, conformal coatings (WO2005/000483; WO2005/123114), foams (WO 2005/012606), electrospun mats (WO 2004/000915), microspheres (PCT/US2007/020789), 3D porous matrices (WO2004/062697), solid blocks (WO2003/056297), microfluidic devices (PCT/US07/83646; PCT/US07/83634), electro-optical devices (PCT/US07/83639), and fibers with diameters ranging from the nanoscale (WO2004/000915) to several centimeters (U.S. Pat. No. 6,902,932). The above mentioned applications and patents are incorporated herein by reference in their entirety. For example, silk fibroin can be processed into thin, mechanically robust films with excellent surface quality and optical transparency, which provides an ideal substrate acting as a mechanical support for high-technology materials, such as thin metal layers and contacts, semiconductor films, dialectic powders, nanoparticles, and the like.

Thus, in various embodiments, a silk matrix can be prepared from an aqueous silk fibroin solution. An aqueous silk fibroin solution can be prepared using techniques known in the art. Suitable processes for preparing silk fibroin solution are disclosed, for example, in U.S. patent application Ser. No. 11/247,358; WO/2005/012606; and WO/2008/127401. See Example 1A for preparation of a silk fibroin solution (~8% w/v). The silk fibroin solution may be diluted to a lower concentration with deionized water, or may be concentrated, for example, to about 30% (w/v), if desired. To obtain a silk fibroin solution with a higher concentration, the silk fibroin solution with a lower concentration may be dialyzed against a hygroscopic polymer, such as PEG, polyethylene oxide, amylose or sericin, for a time period sufficient to result in a desired concentration. For example, an 8% silk fibroin solution may be dialyzed against 10% (w/v) PEG (10,000 g/mol) solution. The dialysis is for a time period sufficient to result in a final concentration of aqueous silk solution between 10-30%. In most cases dialysis for 2-12 hours is sufficient. See, e.g., WO 2005/012606.

The aqueous silk solution can be processed into silk matrices of various material formats, such as electrospun fibers and mats (see Jin et al., Biomacromolecules 3, 1233-39 (2002); WO 2004/0000915), films, conformal coatings or layers (see Jin et al., Biomacromolecules 5, 711-17 (2004); WO 2004/0000915; WO 2005/012606; WO/2006/042287; WO/2007/016524), micro- and nano-spheres (see Wang et al., Biomaterials 31, 1025-35 (2010); WO 2008/118133), hydrogels (see Wang et al., Biomaterials 29, 1054-64 (2008); Yucel et al., Biophys. J. 97, 2044-50 (2009); WO/2005/012606; WO/2008/150861), adhesives (see Leisk et al., Adv. Mat. 22, 711-15 (2010); Yucel et al., J. of Struct. Biol. 170, 406-12 (2010)) and 3-D porous scaffolds (see Nazarov et al., Biomacromolecules 5, 718-26 (2004); WO 2004/062697) for biomaterials, tissue engineering, and cell/drug delivery applications.

In accordance with the invention, different material formats of a silk matrix can be used in producing piezoelectric silk material. In some embodiments, dried, solid material formats, e.g., silk fibers, electrospun mats, scaffolds and films, can be used to produce piezoelectric silk material. In some embodiments, hydrated and/or oriented material formats, such as silk liquid crystals, can be used for the purpose of the invention. In some embodiments, material formats with high water content and an overall isotropic structure, such as silk hydrogels, can be used to produce piezoelectric silk material. However, such material formats may display weaker piezoelectric effect.

In one embodiment, silk films are used in producing piezoelectric silk materials. Silk films can be prepared by drying silk fibroin solution into a film. By way of example, silk films can be prepared by casting the aqueous silk fibroin solution on the substrate. Casting of the silk films can be performed by using any known means, e.g. a spin-coating method, where the silk solution is spin coated onto the substrate to allow the fabrication of thin membranes of non-uniform or uniform height; or simply by pouring silk fibroin solution over the top of the substrate. In some embodiments of the invention, single layer or multiple layers of silk films may be casted on the substrate.

The thickness of the silk matrix, e.g. silk films, can be controlled by changing the concentration and/or volume of the silk solution. In one embodiment, the thickness of a silk film can be controlled by changing the concentration and/or volume of the silk solution deposited on the substrate. The resulting silk film can range from, for example, 2 nm to 1 mm thick. In some embodiments, the film thickness can be in a centimeter range, e.g., at least about 0.1 cm, at least about 0.5 cm, at least about 1 cm, at least about 2 cm, at least about 5 cm, at least about 10 cm or thicker. In some embodiments, depending on the application of the piezoelectric material, the film thickness can be reduced to a micro- or nano-meter range, e.g., at least about 5 nm, at least about 10 nm, at least about 50 nm, at least about 100 nm, at least about 500 nm, at least about 1 µm, at least about 5 µm, at least about 10 µm, at least about 25 µm, at least about 50 µm, at least about 100 µm, at least about 500 µm or at least about 1000 µm. In one embodiment, the film thickness ranges from about 5 nm to about 1000 nm, or from about 10 nm to about 500 nm. In some embodiments, the film thickness has little or low effect on the shear piezoelectric coefficient—an indicator of piezoelectricity. The thickness of the films can be controlled by depositing different numbers of film layers. Suitable processes for preparing silk films are disclosed in, for example WO 2005/012606, WO/2006/042287, and WO/2007/016524. Alternatively, the silk fibroin solution can be spin-coated on a substrate using various concentrations and spin speeds to produce films or layers from about 1 nm to about 300 μm, or from about 1 nm to 500 nm. These silk fibroin films have excellent surface quality and optical transparency. See Example 1B for preparation of silk films.

In some embodiments, a piezoelectric silk film may include a silk matrix. In some embodiments, silk matrices are provided in a form of silk films. Useful silk films may have a thickness of about 1 μm to hundreds of μm. For example, in some embodiments, the thickness of the silk film may be about 10-15 μm. In some embodiments, the thickness of the silk film may be about 60 μm. In some embodiments, the thickness of the silk film may be on the order of hundreds of microns (e.g., about 100 μm, about 200 μm, about 300 μm, about 400 μm, about 500 μm, about 600 μm, about 700 μm, about 800 μm and about 900 μm).

In accordance with the invention, piezoelectric silk material can be produced by a mechanical means. In some embodiments, piezoelectric silk material can be produced by elongating a silk matrix provided herein. In some embodiments, the silk matrix can be elongated in one or more directions. In some embodiments, the silk matrix can be uniaxially elongated. In some embodiments, the silk matrix can be biaxially elongated. By way of example, piezoelectric silk films is prepared by air-drying aqueous, regenerated silk fibroin solutions into films, and elongating the silk films to a desired elongation ratio. In one embodiment, the silk film is elongated in one direction. In some embodiments, the elongation direction can be aligned with an axis of the silk film. In some embodiments, the elongation direction is aligned with an axis of oscillation. For example, without wishing to be bound by theory, an uniaxial elongation of a silk film can result in uniaxial alignment of crystalline silk II domains, producing a silk film with high values of shear piezoelectric coefficient. In other embodiments, the silk film can be elongated from multiple directions. For instance, a multi-axial elongation of a silk film can be performed to decrease silk piezoelectricity. Accordingly, one of skill in the art can select proper elongation direction(s) to generate a silk material with a desired level of piezoelectricity.

Without wishing to be bound by theory, applying an elongation force, e.g., stretching, on a silk matrix to aid in enhancing the degree of uniaxial alignment of silk II crystals can increase piezoelectricity of silk matrix. The elongation ratio λ of a silk matrix is defined herein (e.g., for a silk film) as the ratio of the final length (attained by applying an elongation force to lengthen the silk matrix) to the initial length of the silk matrix (before elongation). In accordance with the invention, the piezoelectricity of a silk material can be increased by elongating a silk matrix (e.g., a silk film or a silk fiber) to a length of at least twice the initial length of the silk matrix (i.e. an elongation ratio λ≥2). In some embodiments, the elongation ratio can be at least greater than 2, greater than 2.7, greater than 3, greater than 4, greater than 5, or greater than 10. In one embodiment, the elongation ratio is at least greater than 2.7.

In embodiments of the invention, a silk material can be elongated at any rate to produce a piezoelectric silk material. In some embodiments, the silk matrix can be elongated at a rate of about 0.5 mm/min to about 20 mm/min, or at a rate of about 5 mm/min to about 15 mm/min. In one embodiment, the silk matrix can be elongated at a rate of about 10 mm/min. In various embodiments, the elongation rate of a silk matrix can affect the piezoelectric property. For example, if the elongation rate is too slow, a high concentration of isotropic crystal domains can form prior to elongation, rendering elongation of a silk matrix impossible. Conversely, if the elongation rate is too fast, insufficient heating ($T<T_G$) can prevent elongation of a silk matrix.

As used herein, the term "elongation", "elongated" or "elongate", in reference to a silk matrix, refers to extending at least one of the dimensions (e.g., length, width, and/or thickness) of an object such as a silk matrix by any methods. Without wishing to be bound by theory, any elongation methods that increase a high degree of molecular alignment and/or silk II crystal structure can be employed in the methods of the invention to enhance silk piezoelectricity. Without limitations, a silk matrix can be elongated, for example, by drawing, pulling, stretching, rolling, compression, extrusion, or a combination thereof. In some embodiments, a silk matrix, e.g., a silk film, can be elongated by drawing. In some embodiments, a silk matrix, e.g., a silk film, can be elongated by compression of the silk matrix with rolling. In other embodiments, a silk matrix, e.g., silk fibers, can be extruded from an aqueous regenerated silk fibroin solution via a coagulation bath, and one or more subsequent steps of draw rolling. This can generate highly-oriented piezoelectric silk fibers. Depending upon the material format of a silk matrix, one of skill in the art can select an appropriate elongation method to produce a piezoelectric silk material.

Different elongation techniques and/or conditions can be used to elongate a silk matrix, e.g., a silk film, to a desired elongation ratio. The choice of an elongation method and/or condition can depend on the physical states or chemical structures the silk matrices. For example, silk matrices, e.g., dried solid-state silk matrices, can be elongated to a desired elongation ratio at an elongation temperature of about the glass transition temperature ($T_G$) of the silk matrices. For a silk matrix in the dried solid state, the glass transition temperature can range from about 100° C. to about 210° C., e.g., from about 170° C. to about 210° C. Accordingly, the elongation temperature can be adjusted to close to this glass transition temperature range of silk matrix. For instance, the elongation temperature for a dried solid silk matrix can range from about 90° C. to about 110° C., or from about 170° C. to about 210° C., or from about 180° C. to about 200° C., or from about 185° C. to about 195° C. Without wishing to be bound by theory, dried silk matrix can be stiff when elongation is processed at temperatures lower than $T_G$; whereas elongating silk films at temperatures much higher than $T_G$ can render the matrix brittle and easy to fracture, possibly due to irreversible β-sheet formation at higher temperatures and subsequent matrix stiffening. See, for instance, Example 2B for selections of elongation temperature for silk film.

However, in some embodiments, this elongation temperature can be adjusted for optimal response depending on the material format, pre-treatment process, physical state, and/or chemical state of the silk matrix. In some embodiments, a silk matrix can be elongated below the glass transition temperature of the dried solid-state silk matrix. For example, a hydrated silk matrix can be elongated below the glass transition temperature of the dried solid-state silk matrix, e.g., at an ambient temperature. In other embodiments, a silk matrix can be elongated above the glass transition temperature of the silk matrix.

In accordance with the invention, the process for producing a piezoelectric material from silk or increasing piezoelectricity in a silk matrix can comprise changing the temperature of a silk matrix, e.g., by heating, cooling or a combination thereof. In some embodiments, the temperature of the silk matrix can be changed from time to time during the process of the invention. In some embodiments, at least one portion of the silk matrix can be subjected to a temperature change. In some embodiments, different parts of the silk matrix can be subjected to various temperature changes. For example, one or more portions of a silk matrix can be subjected to heating while some other portions thereof can be subjected to cooling or no treatment.

In some embodiments, at least a portion of the silk matrix can be heated at a temperature above an ambient temperature, e.g., at a temperature of no less than glass transition temperature of the silk matrix. The heating step can be performed prior to, concurrently with, or after the elongation step. In other embodiments, the local elongation temperature of silk matrices can be changed by local heating. The local elongation temperature of silk matrices can also be changed by locally increasing water content of silk matrices, thereby decreasing the elongation temperature.

In one embodiment, the silk matrix, e.g., a silk film, can be elongated while simultaneously heating locally a portion of the silk matrix, e.g., a silk film, which is being elongated, so that the local heating of the silk matrix prevents extensive crystallization of the silk matrix prior to elongation. This elongation technique is termed herein as "zone-drawing." In one embodiment, a custom setup was produced to enable zone drawing. See Example 1B and FIG. 1B. In such embodiment, the local heating zone is a strip along the width of the silk matrix, e.g., a strip of at least about 0.5 mm thick, at least about 1 mm thick or at least about 2 mm thick.

A temperature control unit can be moved at any rate along a silk matrix, for example, at a rate of about 0.1 mm/s or equivalently 6 mm/min. In some embodiments, the temperature control unit can be moved along a silk matrix at a rate of about 0.1 mm/min to about 50 mm/min, about 0.5 mm/min to about 20 mm/min, or about 1 mm/min to about 15 mm/min. The moving rate of the temperature control unit can affect the actual elongation rate of a silk matrix, which can be calculated by multiplying the speed of the temperature control unit by the instantaneous elongation ratio.

A skilled artisan can optimize the elongation rate and/or moving rate of the temperature control unit to produce a silk matrix with desired piezoelectric property. Methods to characterize piezoelectricity of a material are well known in the art. For example, characterization of molecular structure and possible crystal orientation in silk matrices (e.g., films, rods, etc.) can be performed with Fourier Transform Infrared Spectroscopy (FTIR) and Wide Angle X-ray Diffraction (WAXD), respectively. To correlate the structural transitions with the piezoelectric effect in silk, dynamic mechanical analyzer (DMA) can be coupled with an electrometer to provide an electro-physicochemical basis for silk piezoelectricity for biomedical applications. Any other methods known in the art can be employed in the methods of the invention for characterizing the molecular structure and/or piezoelectric property of a silk matrix.

In one embodiment, silk matrices, e.g., silk films, was zone elongated to a ratio of $\lambda=\sim2.7$ and displayed relatively high dynamic shear piezoelectric coefficients of $d_{14}=-1.5$ pC/N, corresponding to over two orders of magnitude increase in $d_{14}$ due to the matrix elongation. As demonstrated in the Examples, a strong correlation was observed between the increase in the silk II, β-sheet content, and the increase in the elongation ratio, characterized by FTIR spectroscopy ($C_\beta \propto e^{2.5\lambda}$). In the mean time, with the increase in the elongation ratio, there was also a concomitant increasing degree of orientation of β-sheet crystals, detected via WAXD (FWHM=0.22° for $\lambda=\sim2.7$), and an improvement in silk piezoelectricity ($d_{14} \propto e^{2.4\lambda}$) See Example 1B-1F and Examples 2B-2D for detailed characterizations of zone-elongated silk films.

The shear piezoelectric coefficient ($d_{14}$) can depend on factors such as the elongation ratio λ, drawing methods and post-drawing treatment. Typically, increasing elongation ratio can increase the absolute $d_{14}$ values exponentially, keeping the other factors the same. For example, for a dried silk film, the absolute $d_{14}$ value can increase over two orders of magnitude with increasing the elongation ratio, from 0.01 pC/N for $\lambda=1$ (as-dried films) to 1.5 pC/N for $\lambda=\sim2.7$.

In accordance with the invention, a silk matrix of some embodiments can be elongated without any additional heating. For example, with increasing water content in the silk matrix, the glass transition temperature, and therefore the range of the elongation temperature can decrease. In one embodiment, if silk matrices, e.g., films, are completely hydrated, they can be elongated at room temperature due to a decrease in the apparent glass transition temperature. Thus, another aspect of the invention relates to a process for increasing piezoelectricity in a silk matrix at an ambient temperature, e.g., by contacting a silk matrix such as a silk film with an aqueous solvent before, in concurrent, or after elongating the silk matrix. In one embodiment, the silk matrix is contacted with an aqueous solvent before the elongation step. In some embodiments, the silk matrix such as a silk film can be contacted with an aqueous solvent for at least about 30 seconds to about 2 hours, or for at least about 1 minute to about 1 hour, before subjected to elongation. The term "aqueous solvent" as used herein refers to a solvent comprising at least about 30%, at least about 40%, at least about 50%, at least about 60%, at least about 70%, at least about 80%, at least about 90%, at least about 95%, at least about 96%, about 97%, about 98%, about 99% or 100% water. In one embodiment, the aqueous solvent is water.

In one embodiment, water immersion drawing was used to elongate silk matrices to a desired ratio at room temperature. Water-immersion drawing led to a predominantly silk I structure with a lower degree of orientation (FWHM=75°) and a weaker piezoelectric response compared to zone drawing. See Example 1B-1F and Examples 2B-2D for detailed characterizations of water immersion-elongated silk films. In some embodiments, a silk matrix can be elongated, e.g., by water immersion drawing, at a rate of about 0.5 mm/min to about 50 mm/min, or about 5 mm/min to about 25 mm/min. In one embodiment, the silk matrix can be elongated, e.g., by water immersion drawing, at a rate of about 10 mm/min.

In alternative embodiments, elongation methods in organic solvent, e.g., ethanol immersion-drawing, may be also used for the purpose of the invention, due to the high β-sheet content produced by this drawing method (see Kim et al., Sen-I Gakkaishi 53, 365-72 (1997)).

In some embodiments of the invention, the processes described herein do not require annealing at a high temperature (e.g., ~100° C. to ~300° C.) prior to elongating a silk matrix, e.g., a silk film. In some embodiments, the processes described herein can further comprise an additional treatment before, in concurrent, or after the elongation step, e.g., annealing, and methanol treatments, to modify the piezoelectric property of the elongated silk matrix. Methanol post-treatment was previously reported to increase silk piezoelectricity due to the transition of pre-annealed silk fibroin from random coil to β form crystallites. See Ando et al., XXIII Reports on Progress in Polymer Physics in Japan 775 (1980). However, the inventor has discovered that both annealing and methanol post-treatments led to a decrease in the measured shear piezoelectricity values, although both treatments can lead to an increase of the crystalline contents in silk matrix. Different piezoelectric response of the silk matrix to the additional treatment might be attributed to different pre-treatment of the silk matrix prior to the elongation process, and/or different post-treatment conditions, e.g., annealing temperature and pressure, and treatment duration. Alternatively, the drop in silk piezoelectricity values due to these post-treatment processes may be attributed to the decrease in the orientation function with increasing β-sheet content. Post-elongation treatments can lead to a competition between increasing silk II crystallinity and decreasing matrix orientation. Ideally, if the high degree of silk matrix alignment can be preserved, e.g., partially or completely, during the post-elongation treatment, the piezoelectric coefficient values should have increased further. Hence the generation or enhancement of silk piezoelectricity can be a combination of increasing β-sheet crystal content and increasing crystal orientation.

Other methods that increase the degree of the alignment, e.g., uniaxial alignment, of the silk crystals may also be used to enhance the piezoelectricity of silk material. For example, the method may include aligning silk matrix in a magnetic field, e.g., by magnetic poling. The method may also include electronic poling of silk matrix to induce silk II structure or induction of other tensors of the piezoelectric matrix (in addition to the shear tensor) in silk matrix. The method may also include elongating silk matrix in $OH^-$ group rich solvents, or electrospinning and post-electrospinning treatment of silk for oriented, silk II, nanofibrillar mats. The piezoelectricity of silk material can be enhanced by maximizing silk II crystallinity and crystal alignment simultaneously, which may include combining different methods to process silk matrix. For example, electronic or magnetic poling can be combined with using $OH^-$ group rich solvents or electrospinning methods simultaneously or subsequently.

The present invention contemplates that silk polymer alignment may be enhanced by applying charge or an electric field to piezoelectric silk materials. In some embodiments, silk fibroin polymers of the invention include charge modifications. In some embodiments, one or more mutations may be introduced to a silk fibroin polypeptide to modify the net charge and/or distribution of charge across silk fibroin polymer or polymers. For example, any suitable molecular biological techniques may be used. Typically, such mutations are introduced by a recombinant DNA technology, which is widely known in the art. In some embodiments, one or more additional charged (e.g., positively charged and/or negatively charged) amino acid residues may be added to a silk fibroin polypeptide. In some embodiments, one or more charged (e.g., positively charged and/or negatively charged) amino acid residues present in a silk fibroin polypeptide may be removed or replaced. In some embodiments, a modified silk fibroin polypeptide includes naturally occurring or "standard" amino acids and/or non-natural (or unnatural or non-standard) amino acid analogs.

Additionally or alternatively, one or more moieties (e.g., functional substituents) may be added to at least one end of a silk fibroin polypeptide. In some embodiments, such a moiety is used to enhance the alignment of silk fibroin polymers. Useful examples of moieties include, without limitation, charged nano-particles, chromophores, fluorophores, and biopolymers such as oligonucleotides and short polypeptides. Various techniques are known in the art to induce or enhance polymer alignments. Non-limiting examples of such techniques include photoalignment and use of microchannels.

The present invention also contemplates use of template-based alignment of silk fibroin polymers. In some embodiments, a piezoelectric silk film with an improved crystal alignment, resulting in enhanced piezoelectricity, may be produced by casting a silk fibroin solution onto a patterned (e.g., nano-pattern) surface of a substrate. A silk fibroin solution can be prepared. In some embodiments, the silk fibroin solution can be aqueous, although other solvents can be used. An aqueous silk fibroin solution can be between approximately 1.0 wt % and 30 wt % silk. In some embodiments, the solution can be approximately 8.0 wt % silk. Different percent weight solutions can be used to optimize flexibility and/or strength of the silk film while maintaining desired optical functions. Exemplary production of aqueous silk fibroin solution is described in detail in WIPO Publication Number WO 2005/012606 entitled "Concentrated Aqueous Silk Fibroin Solution and Uses Thereof. In some embodiments, a micro-filtration step can be used. For example, the silk fibroin solution can be processed by centrifugation and syringe based micro-filtration. The processes can improve the optical quality and stability of silk films formed from the solution.

A patterned substrate can serve as a mold and/or template in fabricating the silk film with improved crystal alignment for enhanced piezoelectricity. Various substances can be chosen for the substrate, such as a polycarbonate film from Digital Optics Corporation. In some embodiments, the substrate can be an elastomeric stamp or a composite elastomeric stamp. In some embodiments, the substrate can be a glass plate coated with polyimide-poly(methylmethacrylate) (PMMA). In some embodiments, the substrate can include teflon. In some embodiments, the substrate can include a hydrophobic material. Substrates can be coated with a hydrophobic material, such as triethoxysilane, trichlorovinylsilane, or trichlorosilane. In some embodiments, the substrate can be a silicon (Si) wafer. In some embodiments, the substrate can be treated with a silanizing agent to allow for manual detachment of the silk film from the substrate.

Linear patterns can be formed on a surface of the substrate. In some embodiments, the patterns can be formed as recesses on the surface of the substrate. In some embodiments, the patterns can be elevated relative to a surface of the substrate. The patterns can be formed by fabrication techniques, such as standard photolithography techniques, or any other technique as would be appreciated by one of ordinary skill in the art. For example, lithographic techniques that selectively remove portions of substrates can be used. In some embodiments, in e-beam lithography, a beam of electrons can be scanned in a pattern on a substrate.

Casting of the silk fibroin solution onto the substrate may be achieved by any means. For example, the silk fibroin solution may be spin coated onto the surface of the substrate. The silk fibroin solution may be poured over the surface of the substrate. In some embodiments of the invention, single layer or multiple layers of silk films may be casted on the substrate. The silk fibroin solution can be dried to transition the silk fibroin solution to the solid phase.

As the solution dries, the resulting silk film can conform to the linear pattern on the substrate. First, silk may dry to form a surface aligned to the linear pattern. Silk molecules adjacent to the linearly patterned silk surface may align efficiently to the silk surface contacting the substrate, thereby expanding the linear pattern on the substrate in a three-dimensional manner. Additional silk molecules may align efficiently according to the linear pattern followed by prior silk molecules. Thus, silk may substantially self-assemble into a crystal alignment in response to a linear pattern on the surface of a substrate.

In some embodiments, the aqueous silk fibroin solution may be dried for a period of time such as 8-12 or 24 hours. In some embodiments, the solution can be subjected to low heat for expedited drying. Other exemplary drying techniques can include isothermal drying, roller drying, spray drying, and heating techniques.

In some embodiments, a piezoelectric silk film with an improved crystal alignment, resulting in enhanced piezoelectricity, may be produced by exposing a silk fibroin solution to polarized electromagnetic radiation as the solution dries to the solid phase. The polarized electromagnetic radiation may induce the silk to self-align. For example, the polarized radiation may induce the silk to self-align into a substantially crystal structure. As the silk fibroin solution dries to the solid state under the polarized radiation's influence, the solution may form a silk film with a substantially crystal structure. In some examples, polarized radiation may induce the silk to self-align along the polarization vector of the laser. In some embodiments, the polarized radiation may be linearly polarized light from a laser. The laser may emit light of 325 nm, although radiation of any wavelength may be used. The laser may have a power density of 18 mW/cm$^2$, although any power density may be used.

In some embodiments, incorporating at least one other piezoelectric material into the silk film may enhance the silk film's piezoelectricity. For example, piezoelectric materials may be added to the silk fibroin solution used to produce the silk film. Exemplary piezoelectric materials that may be added are quartz, barium titanate, lead zirconate titanate, lithium tantalate, lithium niobate, potassium niobate, sodium tungstate, sodium niobate, sodium potassium niobate, bismuth ferrite, or any combination thereof. Other piezoelectric materials described herein or known to persons of ordinary skill in the art may be added to the silk fibroin solution. In some embodiments, the piezoelectric material(s) may be particles of any size, such as nano-particles. As the silk fibroin solution dries into the solid phase, the added material(s) may become embedded in the resulting silk film.

In some embodiments, a silk film may be doped with one or more piezoelectric materials. Silk films may be doped using any technique, such as implantation or diffusion. For example, a silk film may be doped by implanting additional piezoelectric materials into the film. In some embodiments, piezoelectric materials are doped into silk films via ion implantation. Ions of a piezoelectric material may be produced in a chamber. An accelerator may accelerate the ions to a high speed, and the accelerator may lead to a target chamber, which may house the silk film. Operation of the chamber may accelerate molecules of the piezoelectric material into the silk film, where they may be implanted.

In some embodiments, piezoelectric materials may enter the silk film diffusion. A silk film may be contacted with a piezoelectic material for a period of time. During the contact, molecules of the piezoelectric material may enter the crystal structure of the silk film, where the molecules may be embedded. For example, a piezoelectric material may be dissolved in water or another solvent. The silk film may be immersed in the solution for twenty-four (24) hours, by way of example. Piezoelectric material particles in the solution may permeate the crystal structure of the silk and deposit themselves therein. In some embodiments, a silk film may be contacted with a solid piezoelectric material. During the contact, molecules of the piezoelectric material may diffuse into the crystal structure of the silk film. Although contact for twenty-four (24) hours is described herein, contact for any length of time may be used.

In yet another aspect, embodiments of the invention also provide for piezoelectric silk material prepared from the methods or processes of the invention described in the above embodiments. While a piezoelectric silk material can generate electrical charges in response to a mechanical strain, it can also generate a mechanical force (e.g., sufficient to slightly self-deform the silk material) resulted from an applied electrical field. The converse piezoelectric effect, i.e., electromechanical actuation is a common property of piezoelectric materials.

The piezoelectric silk material of the invention may be in any material formats, such as silk fibers, electrospun fibers, films, mats, 3-D scaffolds, dried gels, spheres, or composites of one or more different formats of silk materials, as described herein.

Silk fibroin in the piezoelectric silk material can be chemically modified with active agents, for example through diazonium or carbodiimide coupling reactions, avidin-biodin interaction, or gene modification and the like, to alter the physical properties and functionalities of the silk protein. See, e.g., PCT/US09/64673; PCT/US10/41615; PCT/US10/42502; U.S. application Ser. No. 12/192,588.

The piezoelectric silk material can also contain one or more biocompatible and/or biodegradable polymers blended with silk fibroin. For example, additional biopolymers, such as chitosan, exhibit desirable mechanical properties, can be processed in water, blended with silk fibroin, and form silk matrix. Other biopolymers, such as collagen, gelatin, agarose, chitin, polyhydroxyalkanoates, pullan, starch (amylose amylopectin), cellulose, alginate, fibronectin, keratin, hyaluronic acid, pectin, polyaspartic acid, polylysin, pectin, dextrans, and related biopolymers, or a combination thereof, may be utilized in specific applications, and synthetic biodegradable polymers such as polyethylene oxide, polyethylene glycol, polylactic acid, polyglycolic acid, polycaprolactone, polyorthoester, polycaprolactone, polyfumarate, polyanhydrides, and related copolymers may also be selectively used. The polymer selected herein to be blended into the silk matrix should not negatively impact the piezoelectricity of the silk matrix.

The piezoelectric silk material of the invention may contain at least one active agent. To form these materials, the silk fibroin can be mixed with an active agent prior to forming the silk matrix and processing the silk matrix, or the active agent can be loaded into the piezoelectric silk matrix after it is formed and processed.

The active agent can represent any material capable of being embedded in the silk matrix. For example, the agent may be a therapeutic agent, or a biological material, such as cells (including stem cells), proteins, peptides, nucleic acids (e.g., DNA, RNA, siRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cell attachment mediators (such as RGD), cytokines, enzymes, small molecules, drugs, dyes, amino acids, vitamins, antioxidants, antibiotics or antimicrobial compounds, anti-inflammation agents, antifungals, viruses, antivirals, toxins, prodrugs, chemotherapeutic agents, hemostatic agents, or combinations thereof. See, e.g., PCT/US09/44117; U.S. Patent Application Ser. No. 61/224,618). The active agent may also be a combination of any of the above-mentioned agents. Encapsulating either a therapeutic agent or biological material, or the combination of them, is desirous because the encapsulated product can be used for numerous biomedical purposes.

In some embodiments, the active agent may also be an organism such as a fungus, plant, animal, bacterium, or a virus (including bacteriophage). Moreover, the active agent may include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above. See also WO 2008/106485; PCT/US2009/059547; WO 2007/103442.

Exemplary antibodies that may be incorporated in silk fibroin include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab. The active agents can also be the combinations of any of the antibodies listed above.

Exemplary antibiotic agents include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents may also be antimicrobial peptides such as defensins, magainin and nisin; or lytic bacteriophage. The antibiotic agents can also be the combinations of any of the agents listed above. See also PCT/US2010/026190.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like. Interactions between components may also be used to functionalize silk fibroin through, for example, specific interaction between avidin and biotin. The active agents can also be the combinations of any of the enzymes listed above. See e.g., PCT/US2010/042585.

When introducing therapeutic agents or biological material into the piezoelectric silk materials, other materials known in the art may also be added with the agent. For instance, it may be desirable to add materials to promote the growth of the agent (for biological materials), promote the functionality of the agent after it is released from the piezoelectric silk material, or increase the agent's ability to survive or retain its efficacy during the period it is embedded in the piezoelectric silk material. Materials known to promote cell growth include cell growth media, such as Dulbecco's Modified Eagle Medium (DMEM), fetal bovine serum (FBS), non-essential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF-I), bone morphogenetic growth factors (BMPs), nerve growth factors, and related proteins may be used. Growth factors are known in the art, see, e.g., Rosen & Thies, Cellular & Molecular Basis Bone Formation & Repair (R.G. Landes Co., Austin, Tex., 1995). Additional options for delivery via the silk-PEGs biomaterial include DNA, siRNA, antisense, plasmids, liposomes and related systems for delivery of genetic materials; peptides and proteins to activate cellular signaling cascades; peptides and proteins to promote mineralization or related events from cells; adhesion peptides and proteins to improve silk-tissue interfaces; antimicrobial peptides; and proteins and related compounds.

Additional biocompatible material may also be blended into the piezoelectric silk material, such as collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, glycerol (see PCT/US2009/060135), and other biocompatible polymers, see WO 2004/0000915. Alternatively, the silk may be mixed with hydroxyapatite particles, see PCT/US08/82487. As noted herein, the silk fibroin may be of recombinant origin, which provides for further modification of the silk such as the inclusion of a fusion polypeptide comprising a fibrous protein domain and a mineralization domain, which are used to form an organic-inorganic composite. These organic-inorganic composites can be constructed from the nano- to the macro-scale depending on the size of the fibrous protein fusion domain used, see WO 2006/076711. See also U.S. patent application Ser. No. 12/192,588.

The piezoelectric silk material with embedded active agents (e.g., therapeutic agents) can be suitable for biodelivery. Techniques for using silk fibroin as a biodelivery device may be found, for example, in U.S. patent application Ser. No. 10/541,182; Ser. No. 11/628,930; Ser. No. 11/664,234; Ser. No. 11/407,373; PCT/US07/020,789; PCT/US08/55072; PCT/US09/44117. Some embodiments of the present invention relate to the utility of piezoelectric silk material with embedded therapeutic agents or biological materials as drug delivery systems for potential utility in medical implants, tissue materials and tissue repairs.

The structure of piezoelectric silk matrix enables a controlled release of the delivery of the embedded active agents (e.g., therapeutic agents or biological materials). Controlled release permits dosages to be administered over time, with controlled release kinetics. In some instances, delivery of the therapeutic agent or biological material is continuous to the site where treatment is needed, for example, over several weeks. Controlled release over time, for example, over several days or weeks, or longer, permits continuous delivery of the therapeutic agent or biological material to obtain preferred treatments. The controlled delivery vehicle is advantageous because it protects the therapeutic agent or biological material from degradation in vivo in body fluids and tissue, for example, by proteases. See, e.g., PCT/US09/44117.

Controlled release of the bioactive agent from the piezoelectric silk matrix may be designed to occur over time, for example, for greater than about 12 hours or 24 hours, inclusive; greater than 1 month or 2 months or 5 months, inclusive. The time of release may be selected, for example, to occur over a time period of about 12 hours to 24 hours, or about 12 hours to 1 week. In another embodiment, release may occur for example on the order of about 1 month to 2 months, inclusive. The controlled release time may be selected based on the condition treated. For example, a particular release profile may be more effective where consistent release and high local dosage are desired.

The piezoelectric silk material of the invention may also comprise one or more other piezoelectric materials. Suitable piezoelectric material include, but are not limited to piezoelectric ceramics such as quartz, barium titanate, lead zirconate titanate, lithium tantalate, lithium niobate, potassium niobate, sodium tungstate, sodium niobate, sodium potassium niobate, bismuth ferrite and composites thereof; piezoelectric polymers and copolymers such as poly(vinylidene fluoride), poly(vinyl fluoride) and their copolymers, polyvinylchloride, polycarbonate, nylons, tetrafluoroethylene, high density polyethylene and poly-L-lactic acid; fibrous proteins such as collagen, gelatin and keratin; polysaccharides such as cellulose and amylase; carbohydrates such as chitin; nucleic acids such as DNAs and RNAs, synthetic polypeptides and poly(amino acids) such as polyalanine, polyleucine, poly-γ-methyl-L-glutamate, poly-γ-methyl-D-glutamate, poly-γ-ethyl-glutamate, poly-γ-benzyl-glutamate, poly-γ-benzyl-aspartate, polyornithine, polyarginine, poly-hydroxyethyl-glutamine and poly-hydroxypropyl-glutamate; polymer foams such as cellular polypropylene and porous polytetrafluoroethylene; optically active polymers such as polypropylene oxide and poly-β-hydroxybutyrate; liquid crystals such as nematic, chlosteric and smectic liquid crystals. Suitable piezoelectric material to be included in silk matrix can also be any combination of one or more of aforementioned piezoelectric material.

The interest in silk fibroin for biotechnological and biomedical applications stems from the highly controllable β-sheet content, exceptional mechanical properties, biocompatibility, and controllable biodegradation rates. See Altman et al., Biomaterials 24, 401-16 (2003); Horan et al., Biomaterials 26, 3385-93 (2005); Ishida et al., Macromolecules 23, 88-94 (1990); Jin & Kaplan, Nature 424, 1057-61 (2003). For example, 3 D silk fibroin scaffolds have shown osteogenic ability in vitro (see Kim et al., Macromol. Biosci. 7, 643-55 (2007); Rockwood et al., "Ingrowth of human mesenchymal stem cells into porous silk particle reinforced silk composite scaffolds: An in vitro study" Acta Biomater., in press, (2010)) and osteopromotive potential in critical sized defects in vivo. See Meinel et al., Bone 39, 922-31 (2006).

Silk piezoelectric material of the invention combines the highly controllable crystallinity and biodegradability, mechanical robustness, and biocompatibility of silk with its controllable electromechanical properties. Such versatile properties of silk piezoelectric material are useful for applications such as sustained engineering of electro-active tissues or related biomaterial applications.

In some embodiments, piezoelectric silk film may be housed in a capsule. The capsule may physically insulate the piezoelectric silk film from the surrounding environment, thereby providing space for the silk film to oscillate in response to perturbations. In some embodiments, the capsule may be substantially rigid. In some embodiments, the capsule may include contacts for forming physical connections with the piezoelectric silk film. For example, the capsule may include conductors. The ends of the piezoelectric silk film may be attached to the conductors.

In some embodiments, substances (e.g., liquid solutions, gases) may enter and/or exit the capsule. For example, the capsule may be permeable. For example, the capsule may have an opening. When a substance enters the capsule, the substance may contact the piezoelectric silk film. In some embodiments, substances may be removed from the capsule by a user (e.g., the user may drain the substance by pouring the substance from an opening in the capsule). In some embodiments, the capsule may be substantially hermetically sealed.

In some embodiments, the capsule may comprise a biocompatible material. For example, the capsule may comprise a biopolymer such as silk, collagen, chitosan, or any other biocompatible material described herein or would be understood by one of ordinary skill in the art. In some embodiments, the capsule may comprise metal. The metal may include gold, silver, or aluminum. The metal may include any metal as would be understood by one of ordinary skill in the art In some embodiments, piezoelectric silk material can be used in sensors. Silk-based piezoelectric sensors may be used to sense (e.g., detect and/or determine), without limitation, pressure, force, acceleration, strain, or combination thereof. In some embodiments, silk-based piezoelectric devices such as silk-based piezoelectric sensors are used in vivo or in situ. For example, a piezoelectric silk element can be positioned within a cardiac assistance device, e.g., a pulse generator or a pacemaker, to serve as a dynamic strain gauge and sense tissue vibration transmitted from the surrounding heart tissue. In addition to sensing mechanical force, the piezoelectric silk element may be able to detect sound. For example, ultrasound may be sufficient to deflect or deform a piezoelectric silk film, which in turn generate electrical signals. Thus, piezoelectric silk materials can be used in ultrasound transducers for high-frequency biomedical imaging in the fields of ophthalmology, dermatology and intravascular imaging, such as echocardiography.

In some embodiments, piezoelectric silk material can be manufactured and/or used in conjunction with biologically active compounds, e.g., agents or drugs. In some embodiments, for example, one or more agents may be incorporated into silk materials used to make a silk-based piezoelectric element or device. In some embodiments, the piezoelectric silk material can be coated with an agent, e.g., antibodies, peptides, oligonucleotides, proteins, cells, or fragments thereof, for use as a silk-based piezoelectric device or a biosensor. For example, when a piezoelectric silk material coated with glucose-binding proteins is exposed to a glucose-containing biological sample, the binding of the glucose to glucose-binding proteins may change the conformation of the glucose-binding proteins, which in turn deform the piezoelectric silk material to generate an electric signal. Hence, glucose concentration can be determined based upon the magnitude of the induced electric signal. Since piezoelectric-based biosensors can be miniaturized, they can be suited for use as implantable biosensors, e.g., glucose biosensors as needed in diabetes.

In some embodiments, the piezoelectric silk material can be used as a voltage source. For example, using a piezoelectric silk element to harvest energy from the heart could allow a cardiac assistance device, e.g., a pacemaker, to recharge a battery as needed in the device, or to work even without a battery. In some embodiments, a piezoelectric silk material can be used to generate energy, e.g., by bending it, to power a handheld equipment.

In some embodiments, the piezoelectric silk material can be used as actuators, e.g., to control volumetric flow rate of a pump. For example, in a micropump, a piezoelectric silk component can be attached to a flexible membrane placed above the opening of a fluid-filled chamber. A voltage applied to the piezoelectric silk component can cause it to deform, which in turn induces a bending stress on the flexible membrane and pumps the fluid through an outlet of the chamber. Hence, these micropumps can be used in biomedical applications, e.g., micropumps on a lab-on-a-chip device for drug delivery.

In alternative embodiments, the piezoelectric silk material used in micropumps can be further coated with an agent, e.g., antibodies, peptides, oligonucleotides, proteins, cells, or fragments thereof. By way of example, the piezoelectric silk material used in micropumps can be coated with glucose-binding proteins. Hence, the interaction of glucose with glucose-binding proteins can control the deformation of piezoelectric silk material and thus the flexible membrane to regulate the release of insulin based upon glucose concentration. It is envisioned that the piezoelectric silk materials can be integrated into a sensor-drug delivery device, e.g., a closed-loop insulin device.

In some embodiments, a sensor may include a piezoelectric silk film housed in a silk capsule. The piezoelectric silk film may be contain at least one active agent, such as any of the agents described herein. In some embodiments, metal (e.g., gold) may be sputtered onto opposite sides of the piezoelectric silk film. In some embodiments, metal connectors may be attached to opposite ends of the piezoelectric silk film. The silk capsule may include metal contacts that connect to the sputtered metal or the connectors attached to the film's opposite ends.

In some embodiments, the metal contacts of the capsule may communicate with a power source (e.g., proximate to a wireless coil, connected to a regular voltage supply). In some embodiments, the metal contacts of the capsule may connect to a dynamic mechanical analyzer (DMA), an electrometer, or both. The DMA and/or electrometer may send signals regarding the piezoelectric silk film to a computer for analysis.

In some embodiments, at least one reference signal for the piezoelectric silk film may be obtained. A power source may supply a voltage to the ends of the piezoelectric silk film. The silk film may deform in response to the voltage. The dynamic mechanical analyzer may calculate a strain signal, which may include oscillations, based on the silk film's deformation and output the strain signal to the computer. The computer store the relationship between the voltage applied to the piezoelectric silk film and the strain signal the silk film produces, in response.

The piezoelectric silk film may be contacted with a test substance. The test substance may include an analyte for detection. In some embodiments, at least one agent incorporated into the piezoelectric silk film may react with the analyte. The reaction between the agent and the analyte may alter the behavior of the piezoelectric silk film. The power source may supply a voltage to the ends of the piezoelectric silk film after the film has been contacted with the test substance. The electrometer may output a strain signal to the computer. Based on a comparison between the received strain signal and the reference signal, the computer may determine if the analyte of interest is present in the test substance. In some embodiments, the computer may determine an analyte of interest is present when the frequency of oscillation in the strain signal has changed by a predetermined threshold.

In some embodiments, the piezoelectic silk film may be used to harvest and store energy from ambient perturbations. For example, the piezoelectric silk film may be housed in a capsule or half-capsule. Metal connectors attached the to silk films' ends may be connected to a capacitor, by way of example. As the silk film is exposed to ambient perturbations (e.g., sound, air pressure), the piezoelectric silk film may generate charge. The silk film may store charge on the capacitor. In some embodiments, the silk film may be used to recharge a battery. In some embodiments, the capacitor may be connected to an external device that harvests the charged produced by the piezoelectric silk film and aggregates the charge with other collected charges.

In various embodiments, piezoelectric silk-based materials of the invention can be sized to match various needs, e.g., biomedical applications described herein.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1. Materials and Methods

1A. Preparation of Aqueous Silk Fibroin Solutions and Silk Films

Silk fibroin aqueous solutions were prepared as previously described. See Nazarov et al., 2004. Briefly, *Bombyx mori* cocoons were cleaned and cut into small pieces. In a subsequent degumming process, sericin, a water-soluble glycoprotein bound to raw silk fibroin filaments, was removed from the silk strands by boiling *Bombyx mori* cocoons in an aqueous solution of 0.02 M sodium carbonate for 30 minutes to 60 minutes. Thereafter, the remaining silk fibroin bundle was rinsed thoroughly in deionized (DI) water ($\rho$=18.2 M$\Omega$) to extract the glue-like sericin proteins and allowed to dry overnight. The dried silk fibroin was dissolved in an aqueous solution containing 9.3 M LiBr at room temperature or heated at 60° C. for 4 hours. The silk fibroin solution was dialyzed against DI water using Slide-A-Lyzer® 3.5K MWCO dialysis cassettes (Fisher Scientific, Pittsburgh, Pa.) for 2 days to remove the residual salt. The final concentration of the silk fibroin in the solution was approximately 8 wt %.

In a typical experiment, ~100-200 µm thick silk fibroin films were prepared by air-drying an appropriate volume of aqueous, regenerated silk fibroin solution on a 100 mm-diameter polystyrene Petri dishes (Fisher Scientific, Pittsburgh, Pa.). Film thicknesses were measured using a micrometer with a resolution to 0.25 µm.

1B. Film Processing

Zone drawing: A custom setup was used to draw silk films at a high temperature. See FIG. 1B for a schematic of the custom set of for zone drawing. Samples (e.g., silk films with a typical dimension: 50 mm long and 20 mm wide) were locally equilibrated at T=190±3° C. ($\approx T_G$, measured using dynamic mechanical analyzer at an oscillation frequency of $\delta$=1 Hz). The local heating of sample films was performed by using a temperature control block consisting of two 2 mm-thick, narrow zone heating elements and cooling fans that flanked the sample film from both sides. The heating elements enabled local heating of the sample film and prevented extensive β-sheet crystallization prior to the film drawing. The temperature block was controlled via a temperature controller (PXR4, Fuji Electric Systems Co., Ltd, Tokyo, Japan). A linear motion system (Specialty Motions, Inc., Corona, Calif.) was employed to move the temperature control block along the length of the sample film at approximately 0.1 mm/s, while approximately 5-10 MPa of stress was simultaneously applied on the film using a pulley to enable film drawing to a desired elongation ratio $\lambda$ ($\lambda$=final length/initial length).

Water immersion drawing: Alternatively, sample films could be elongated at room temperature after immersion in DI water, due to subsequent film softening. In particular, silk films were kept in DI water for up to 30 minutes. Immediately after hydration, a constant normal elongation rate of 10 mm/min was applied on the silk films using a dynamic mechanical analyzer (RSA III, TA Instruments, New Castle, Del.).

Post-drawing treatment: Control experiments may be performed by subjecting elongated films to further treatments, such as high temperature (200° C.) annealing, in air or in vacuum, for up to one hour, or methanol treatment, i.e., incubation of the elongated films in methanol, for up to two days.

1C. Fourier Transform Infrared Spectroscopy

The molecular conformation of silk fibroin films was investigated using a JASCO FTIR 6200 spectrometer (JASCO, Tokyo, Japan), equipped with a MIRacle™ (PIKE Technologies, Madison, Wis.) attenuated total reflection (ATR) Ge crystal cell in the reflection mode. Air background measurements were taken immediately prior to sample loading and were subtracted from the sample reading. Each reported spectrum was the average of 32 scans collected at a resolution of 4 cm$^{-1}$, for a wave number ranging from 400 cm$^{-1}$ to 4000 cm$^{-1}$.

1D. Wide Angle X-ray Diffraction

Wide angle X-ray diffraction was performed at room temperature on a Bruker AXS GADDS system (Bruker AXS Inc., Madison, Wis.), equipped with a two-dimensional gas-filled wire detector. Intensity was collected for 30 minutes using a 0.5 mm collimator while the generator was operated at 40 kV and 20 mA. The wavelength was 0.1542 nm (Cu-K$_\alpha$) and the scattering angle, 2θ, was calibrated using sodelite powder as a reference standard. Samples were examined in the transmission mode with the drawing (or orientation) direction of samples placed approximately horizontally, i.e., parallel to the level ground.

1E. Dynamic Mechanical Measurements

The dynamic mechanical properties of silk films were probed using a dynamic mechanical analyzer (RSAIII, TA Instruments). Dynamic temperature sweeps were collected between room temperature and 200° C. at an oscillation frequency of δ=1 Hz and a heating rate of 5° C./min to determine the apparent $T_G$. Subsequently, dynamic time sweeps were collected at a low-strain amplitude (γ=0.01-0.05%) at temperatures close to the previously reported β-sheet crystallization temperatures of silk fibroin (~200° C.) (see Hu et al., Macromolecules 42, 2079-87 (2009)) to follow the temporal changes in mechanical properties due to annealing.

1F. Dynamic Piezoelectric Measurements

Figure 4A:
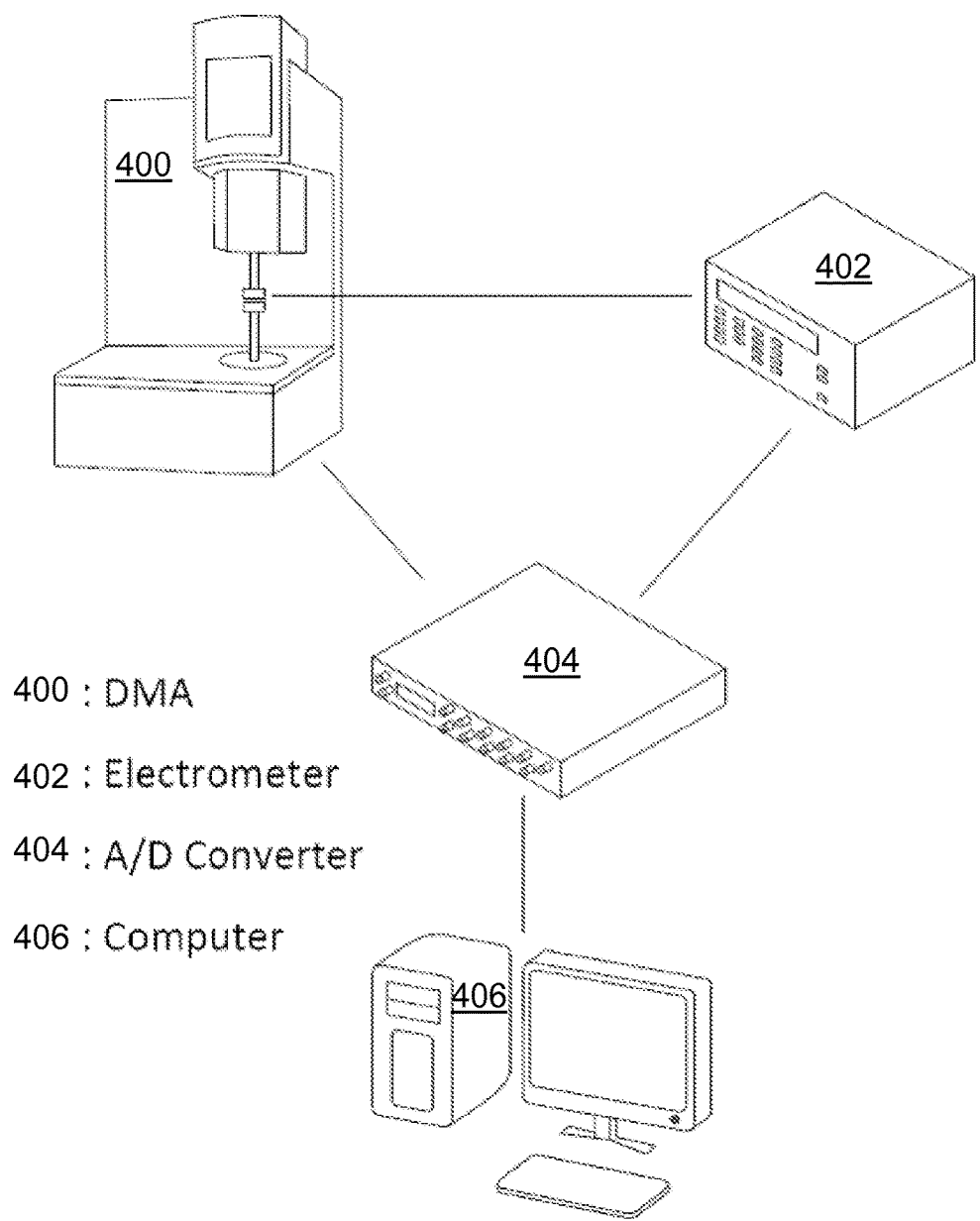
FIG. 4A is a schematic of the custom setup for piezoelectric measurements: the strain signal from a DMA (400) and the current reading from an electrometer (402) were fed through an A/D converter (404) to a computer (406).

A schematic of a custom setup for piezoelectric measurements is shown in FIG. 4A. For piezoelectric coefficient measurements, regular octagonal shaped film samples with a span of 5 or 10 mm were cut from rectangular shaped silk films (which can include the films that are as-dried, elongated, or post-drawing processed) using titanium scissors. Octagonal shaped samples enabled collection of piezoelectric measurements as a function of 8 measuring angles (θ=0, ±π/4, ±π/2, ±3π/4, π). The measuring angle is defined as the angle between the direction of the applied strain and the drawing (or orientation) direction. Prior to the measurements, 200 nm thick gold layers were sputter-coated on both sides of film surfaces. A dynamic mechanical analyzer (DMA) (RSAIII, TA Instruments) and a programmable electrometer (Model 617, Keithley Instruments Inc, Cleveland, Ohio) were employed to measure the dynamic piezoelectric coefficient. The fixtures of the DMA were covered with a high-temperature tape to prevent electrical shortage. Electrical contacts were taken from both sides of film surfaces to the electrometer. Each side of film was in electrical contact with a different terminal of the electrometer through conductive leads. This setup allowed measurements of the current perpendicular to the film plane, generated by using the electrometer, in response to the sinusoidal displacement parallel to the film plane, applied by using the DMA. Under normal operation, the RheoCorr software (TA Instruments) allows monitoring the real-time dynamic strain ($\epsilon$) and stress ($\sigma^*$) signals from the DMA through a DAQ-Pad™-6020E A/D converter (National Instruments, Austin, Tex.). The stress and strain signals are cross-correlated to calculate the dynamic tensile modulus ($E^*=\sigma^*/\epsilon=E'+iE''$) and the loss tangent ($E''/E'$). To conduct piezoelectric measurements, the current output from the electrometer (instead of the stress output from the DMA in normal operation) was interfaced with the RheoCorr software through the A/D converter. In this manner, the RheoCorr software was able to directly display the sinusoidal waveform of the applied displacement and an apparent stress response, which was a result due to the current generated in the film sample. The software then calculated an apparent complex stress from the waveform data. Thus, it was possible to convert the apparent complex stress output from the RheoCorr software into a complex piezoelectric coefficient ($d^*=d'-id''$), using a correction factor. All reported piezoelectric measurements were carried out at $\delta=0.5$ Hz frequency and at low-strain amplitude within the linear stress-strain regime. The apparent dynamic piezoelectric coefficient was calculated from (see Hayakawa & Wada, Advances in Polymer Science, Vol. 11, Springer, New York, 1973, 1-56):

$$|d^*| = \left(\frac{I}{A_E}\right) / \left(\frac{F}{A_{XS}}\right) (A/m^2)/(N/m^2), \quad (1)$$

where I is current generated perpendicular to the film plane, $A_E$ is the electrode area, F is the force applied in the plane of the film, and $A_{XS}$ is the cross-sectional area. For measuring angle dependence of the piezoelectric coefficient ($d(\theta)$ vs. $\theta$) experiments, the error in $\theta$ ($\xi_\theta$) was estimated using a sinusoidal fit of the form $$d(\theta) = d_{max} \sin\left(\frac{\theta}{2} + \xi_\theta\right)$$

with the IGOR Pro software (Wavemetrics, Inc., Lake Oswego, Oreg.), where $d_{max}$ is the maximum value of the apparent piezoelectric coefficient ($d=d_{max}$ for $\theta=\pi/4$). For a uniaxially oriented polymer film with class $D_\infty$, 3×6 piezoelectric coefficient matrix ($d_{14}=-d_{25}$, $d_{ij}=0$ otherwise) (see Fukada, Q. Rev. Biophys. 16, 59-87 (1983)), the shear piezoelectric coefficient, $d_{14}$, can be calculated using (see Fukada, Ferroelectrics 60, 285-96 (1984)):

$$d_{14} = \frac{2d_{max}}{\sin(2\theta)} \quad (2)$$

Example 2. Results and Discussion

2A. Film Processing

Figure 1B:
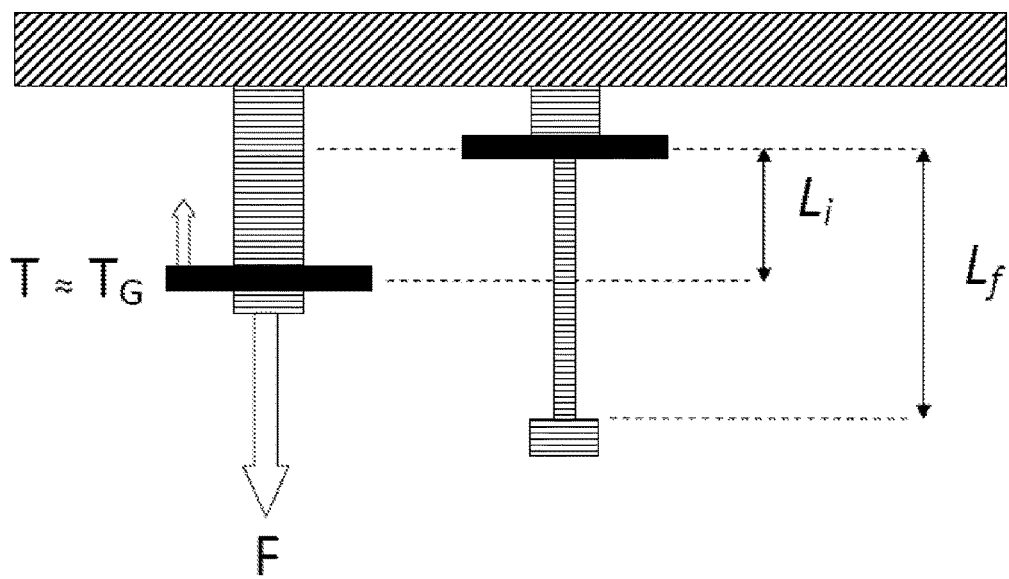
FIG. 1B is a schematic of one embodiment of the custom zone-drawing setup for processing silk matrix, e.g., silk films.
Figure 1B:
Figure 1B:
Figure 8A:
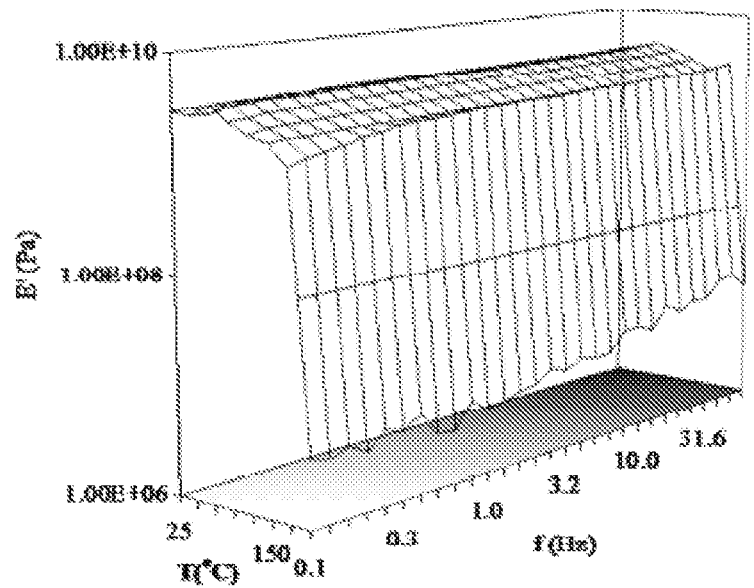
FIGS. 8A-8B show the results of DMA measurements on a 100 μm-thick silk film.
Figure 8B:
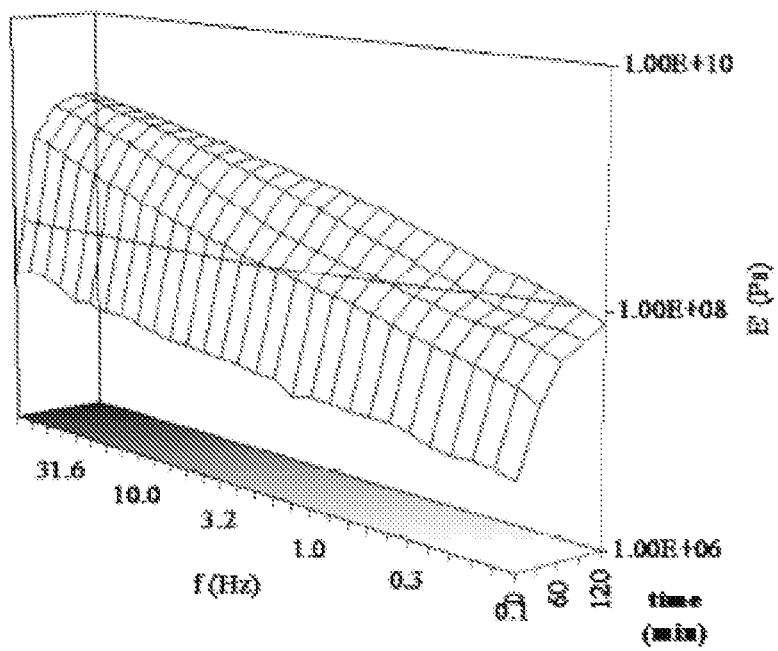

Dynamic mechanical analysis was employed to establish a suitable temperature for zone-drawing silk fibroin films. FIG. 1A shows typical results of temperature sweeps of the complex dynamic tensile modulus, $E^*=E^*+iE''$ (where E is the storage modulus and E" is the loss modulus) and the loss tangent, tan ($\delta$)=E"/E' for silk fibroin films. At a heating rate of 5° C./min, for temperature ranging from room temperature up to approximately 170° C., $E^*$ was essentially constant upon the temperature change and was frequency independent (see, e.g., FIG. 8A); for T>170° C., there was a sharp decrease in $E^*$ values that indicated an onset of a "glass transition". At this heating rate, tan ($\delta$) peaked at 190° C., suggesting a "glass transition temperature" or $T_G$ (FIG. 1A). Typically, silk films can be stiff for zone drawing at temperatures lower than $T_G$; whereas drawing silk films at temperatures much higher than $T_G$ may render the film brittle and easy to fracture, possibly due to irreversible β-sheet formation at higher temperatures and subsequent film stiffening (see e.g., FIG. 8B: the time evolution of frequency sweeps of $E^*$ during a 200° C. annealing of silk films). Accordingly, a temperature of 190±3° C. was used for silk fibroin zone drawing. Using a custom zone drawing setup (FIG. 1B), silk films were elongated up to an elongation ratio of $\lambda=2.7$.

Alternatively, silk films could be elongated at room temperature after immersion of as-dried films in water, which can soften the films. This decrease in film stiffness may be at least partially due to a decrease in the effective $T_G$ because of the film hydration. See Agarwal et al., J. Appl. Polym. Sci. 63, 401-10 (1997); Hu et al., Macromolecules 41, 3939-48 (2008). After water immersion, films taken out from water could be easily elongated at a constant elongation rate of 10 mm/min using a DMA. By this technique, silk films were elongated up to an elongation ratio of $\lambda=2.0$, while higher elongation ratios may result in cracks in silk films, possibly due to film drying and subsequent stiffening. Further, drawing silk films while still immersed in water may prevent films from drying and stiffening, and may allow higher elongation ratios.

2B. Structure

Figure 2A:
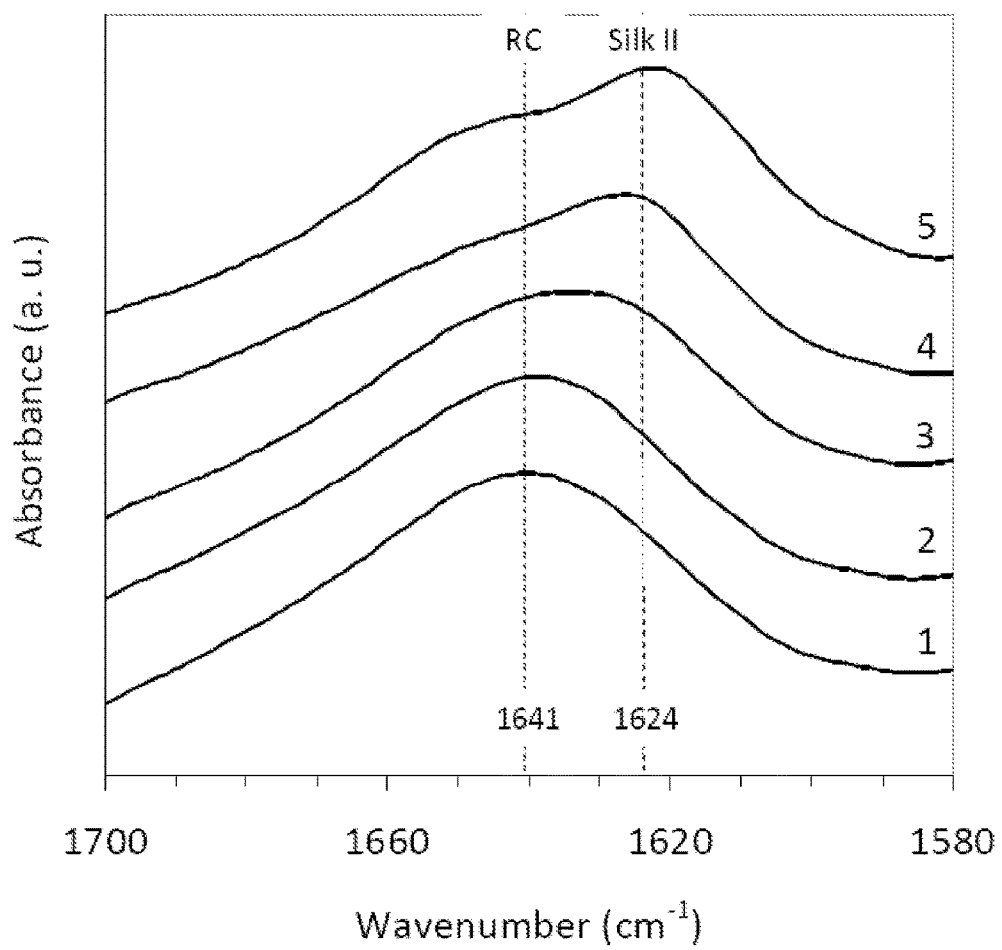
FIGS. 2A-2B are graphs demonstrating the structural characteristics of silk film as a function of elongation ratio, elongation method and post-elongation treatment, characterized by Fourier Transform Infrared Spectroscopy.

FTIR spectroscopy was employed to quantify possible effects of processing parameters (elongation ratio, drawing method and post-drawing treatment) on the overall molecular conformation (FIG. 2) according to the C=O stretch vibrational band assigned for common protein secondary structures in the amide I region (1600-1700 cm$^{-1}$). See Hu et al., Macromolecules 39, 6161-70 (2006); Jung, J. Mol. Recognit., 13, 325-51 (2000); Tretinnikov & Tamada, Langmuir 17, 7406-13 (2001). As-dried silk fibroin films displayed broad IR absorption with a single peak at 1641 cm$^{-1}$ in the amide I region (FIG. 2A), which is typical for a predominantly amorphous conformation. See Hu et al., 2006. For zone-elongated films, the peak position progressively shifted to lower wave numbers with increasing elongation ratio, and eventually a second peak appeared at 1624 cm$^{-1}$ for elongation ratio of $\lambda=2.7$, indicating the formation of silk II type, β-sheet rich structures. See Hu et al., 2009; Hu et al., 2006. Consequently, the ratio of the absorbance at 1624 cm$^{-1}$ to that at 1641 cm$^{-1}$ ($C_\beta=A_{1624}/A_{1641}$) was used to estimate the increase in silk II conformation, i.e., β-sheet content, when increasing the elongation ratio. Corresponding $C_\beta$ values were 0.73, 0.76, 0.93 and 1.13 for elongation ratio $\lambda=1.0$, 1.5, 2.0 and 2.7, respectively, for zone drawing.

$C_\beta$ values were also normalized with respect to the lowest ($C_{\beta,min}$) and highest values ($C_{\beta,max}$) using $$C'_{\beta,i} = \frac{C_{\beta,max} - C_{\beta,i}}{C_{\beta,max} - C_{\beta,min}}.$$

The normalization can be used to evaluate the correlation between the β-sheet content and the piezoelectric coefficient of the silk films.

FTIR spectra collected after two post-drawing processing steps, namely, annealing of silk films at 200° C. for one hour ($C_\beta$=1.13 for λ=2.0) (FIG. 2A) and immersion of films in methanol for two days ($C_\beta$=1.22 for λ=2.0), indicated that both treatments led to a further increase in the silk II conformation, i.e., β-sheet content, compared to zone-elongated films without post-drawing treatment. The increase in $C_\beta$ with either treatment could be beneficial for potential biomedical applications that require low biodegradation rates. Annealing the elongated silk films at 200° C. for extended periods may render the films brittle.

Figure 2B:
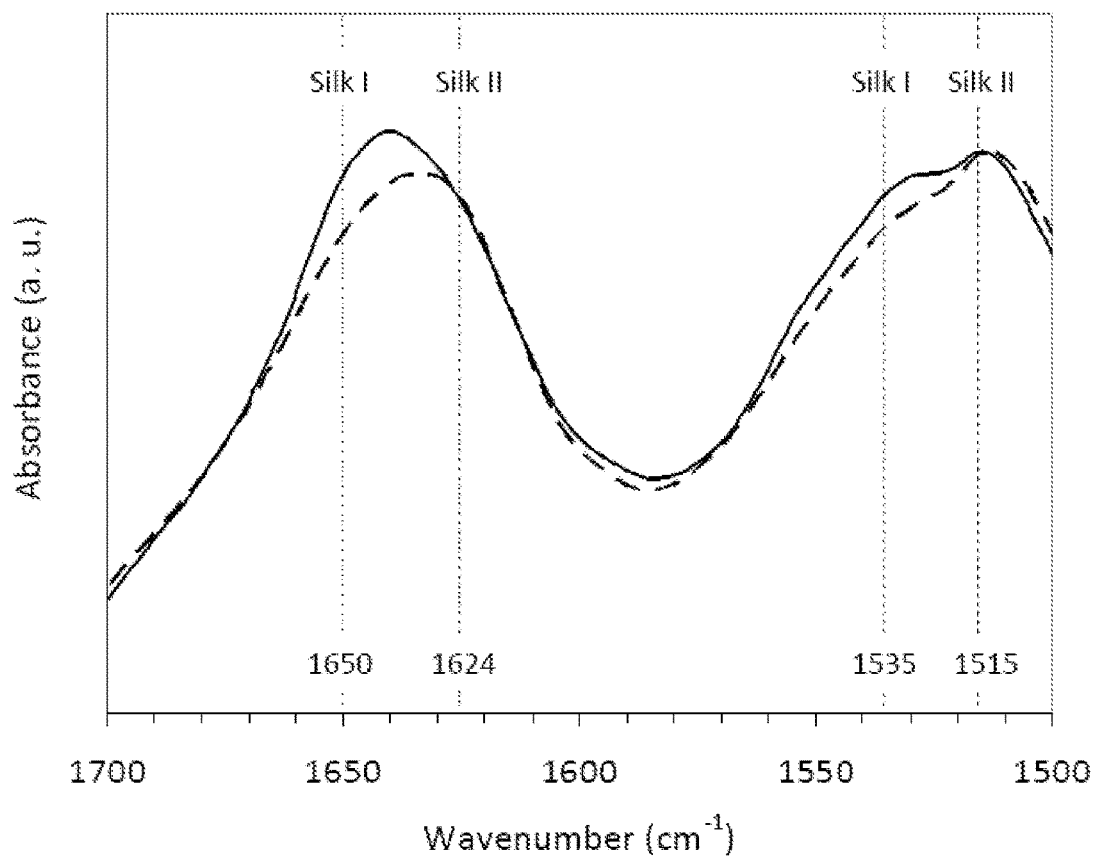
Figure 3A:
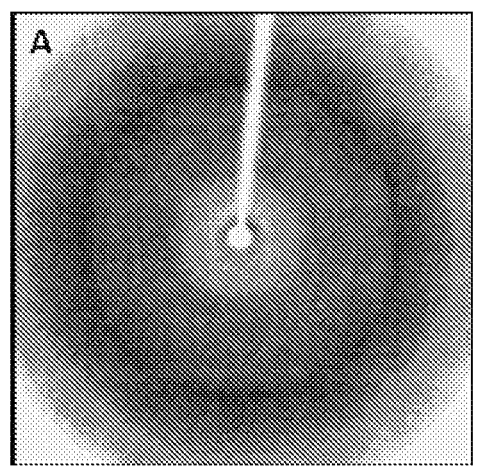
FIGS. 3A-3D show two dimensional Wide Angle X-ray Diffraction plots collected from silk fibroin films as-dried (FIG. 3A), or processed by zone-drawing ($\lambda$=2.7, FIG. 3B), annealing (200° C. for 1 hr) (FIG. 3C), or zone drawing ($\lambda$=2.7) followed by annealing (200° C. for 1 hr) (FIG. 3D). The elongation direction relative to the scattering data in FIGS. 3B and 3D is indicated by the arrow in FIG. 3A. Miller indices are included for crystal reflections in FIG. 3D.
Figure 3B:
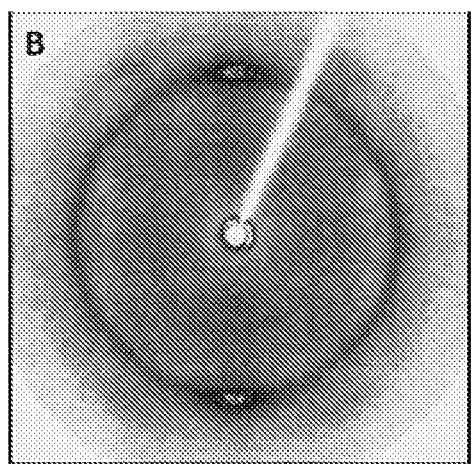
Figure 3C:
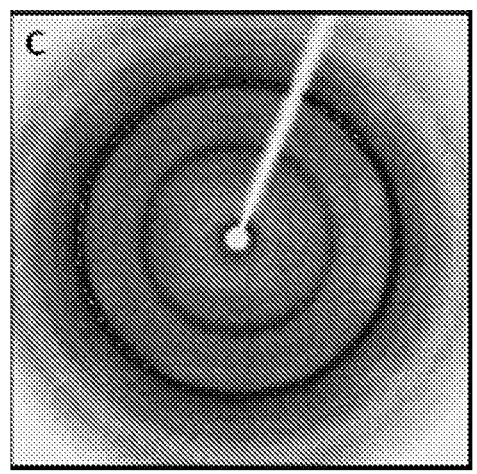
Figure 3D:
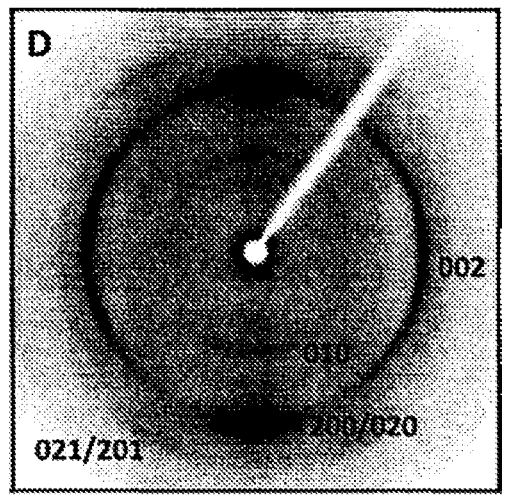

Water immersion drawing, different from zone drawing, did not lead to a significant increase in the apparent β-sheet content (FIG. 2B). Water immersion-elongated films showed an amide I peak at 1641 cm$^{-1}$ and a shoulder at 1650 cm$^{-1}$, in addition to an amide II peak at 1533 cm$^{-1}$, suggesting a silk I-type structure (see Wilson et al., Biophys. J. 78, 2690-701 (2000)), i.e., a less extended, crystalline polymorph of silk II.

Wide Angle X-ray Diffraction (WAXD) was employed to characterize possible film crystallinity and orientation due to drawing and post-draw treatment (FIG. 3). X-ray patterns showed a transition from an essentially amorphous, isotropic structure from as-dried films (diffuse halo in FIG. 3A) into a β-sheet crystal structure (silk II) after zone-drawing (λ=2.7) (FIG. 3B). Annealing of both as-dried (FIG. 3C) and zone-elongated films (FIG. 3D) at 200° C. for one hour led to an increase in the degree of crystallinity. Miller plane indices for silk II, β-sheet crystal peaks were labeled in FIG. 3D with corresponding d-spacings of 0.95 nm (010), 0.43 nm (200)/(020), 0.37 nm (021)/(201) and 0.35 nm (002). See Shen et al., Macromolecules, 31, 8857-64 (1998). Methanol treatment of silk films for 48 hours resulted in an increase in film crystallinity similar to that due to annealing.

Water immersion-elongated films (λ=2.0) showed a strong reflection at 0.72 nm attributable to the silk I form. See Asakura et al., Macromolecules, 18, 1841-45 (1985). At the same elongation ratio (λ=2.0), the peak positions for zone-elongated films indicated a mixture of silk I (0.72 nm) and silk II (0.37 nm and 0.95 nm (weak)) structures.

The degree of uniaxial, crystal orientation due to film drawing was quantified from the full-width at half maxima (FWHM) calculated from scattered intensity versus azimuthal angle plots. Peak widths for films elongated using different techniques to the same elongation ratio (λ=2.0) were compared, and the results indicated that a considerably higher degree of crystalline orientation presented in films processed by zone drawing (FWHM=27° as compared to in films processed by water immersion drawing (FWHM=75°). The degree of orientation increased further for zone-elongated films with increasing the elongation ratio (FWHM=22° for λ=2.7)

2C. Piezoelectric Measurements

Figure 4B:
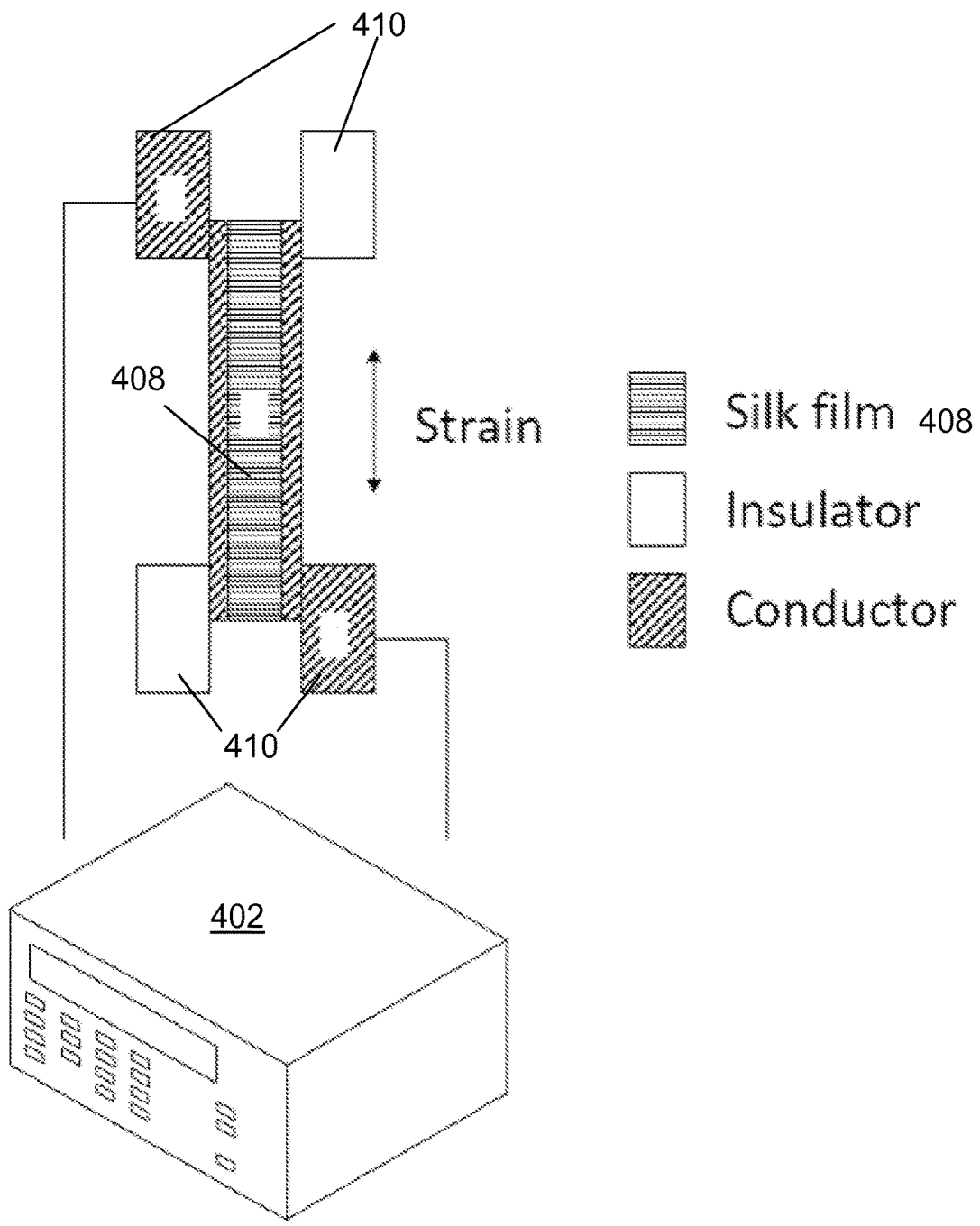
FIG. 4B is a schematic showing the cross-sectional view of a silk film (408) placed between DMA fixtures (410), which are then coupled to the electrometer (402).

A custom setup was employed for piezoelectric measurements by feeding the strain signal from a DMA 400 and feeding the current signal from an electrometer 402 to a computer 406 through an A/D converter 404 (FIG. 4A). A gold sputtered silk fibroin film was placed between the fixtures of the DMA. Each film surface was connected to a different terminal of the electrometer through conductive leads, while electrically insulating the opposite film surface (FIG. 4B). In this manner, the dynamic current generated perpendicular to the film plane (i.e., along the thickness of the film) in response to the application of a sinusoidal strain in the plane of the film could be measured.

Figure 4C:
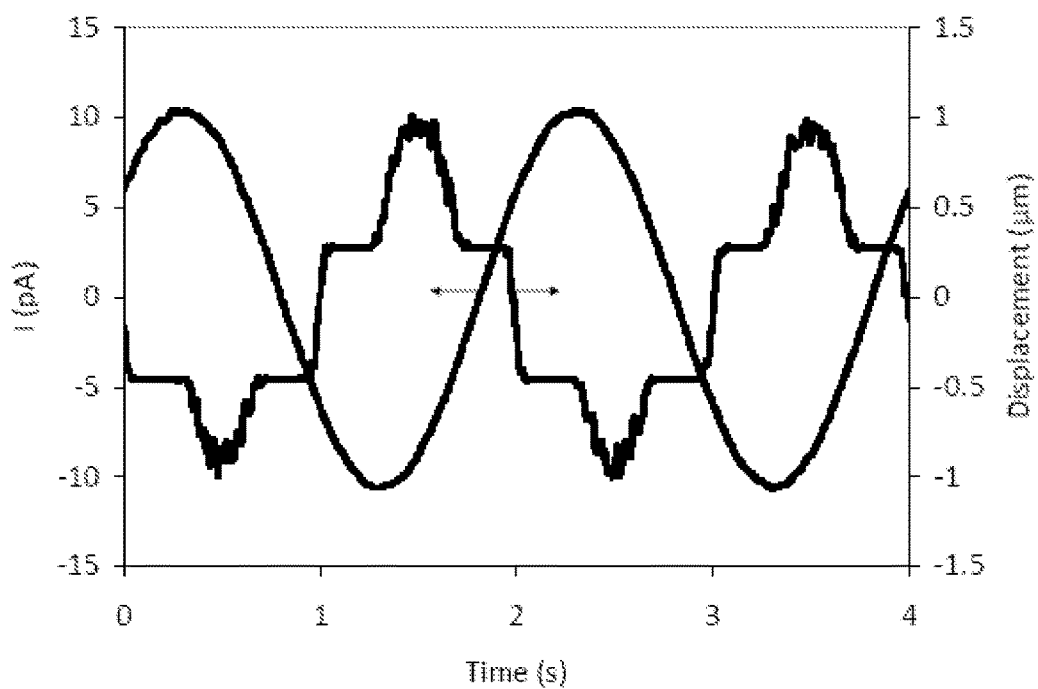
FIG. 4C is a graph showing the results of piezoelectric measurements of an elongated silk film at an elongation ratio of $\lambda$=2.7, the results containing raw waveform data showing the sinusoidally applied displacement and the generated complex polarization for the silk film at measuring angle $\theta = \pi/4$.

FIG. 4C shows the waveform data for the time evolution of the piezoelectric current in a zone-elongated silk fibroin film (λ=2.7). For instance, a sinusoidal strain was applied at a measurement angle, θ=π/4, where θ is defined as the angle between the direction of strain applied by the DMA and the film drawing (orientation) direction in the film plane. A normal displacement of ±1 μm (corresponding to a strain of 0.04%) at 0.5 Hz resulted in a shear piezoelectric polarization value of ±10 pC and a potential difference of ±20 mV, a value that may be sufficient to affect certain cell behavior. See Levin, Trends Cell Biol. 17, 261-70 (2007).

2D. Shear Piezoelectricity and Structure

Figure 5:
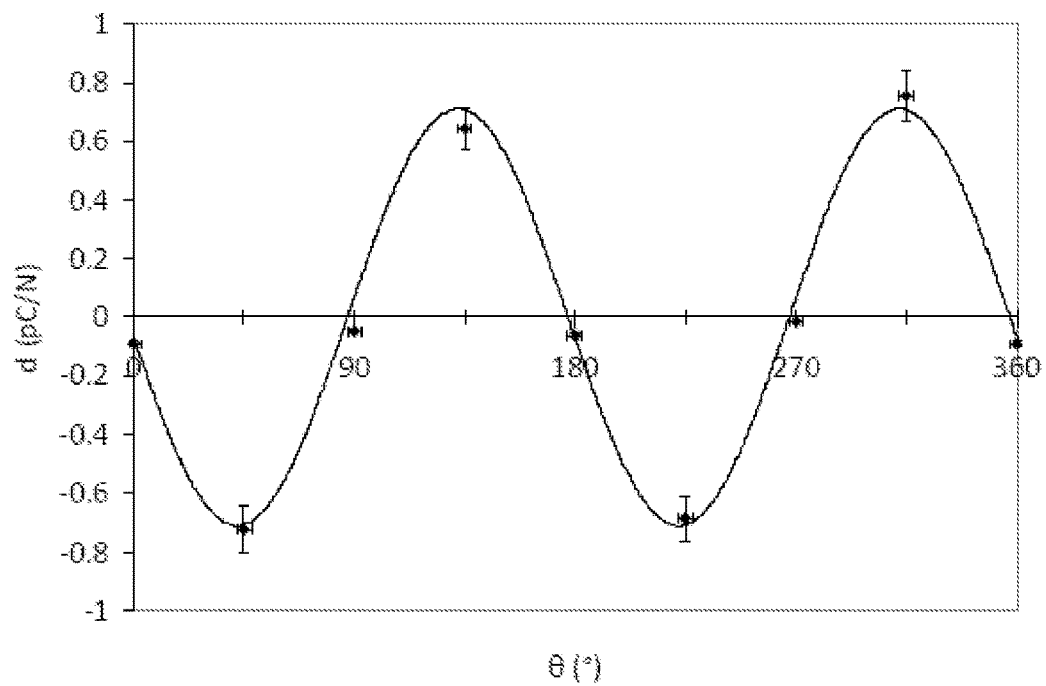
FIG. 5 is a graph showing the apparent piezoelectric response of an elongated silk film at an elongation ratio of $\lambda$=2.7, as a function of the measurement angle $\theta$ (n=3).

FIG. 5 shows the dependence of the piezoelectric constant, d on θ. For $$\theta = \frac{2n-1}{4}\pi$$

(i.e. the shear direction), $d=d_{max}$, while $d \to 0$ for $$\theta = \frac{n-1}{2}\pi$$

(for integer values of n). The maxima in the piezoelectric coefficient in the shear direction could arise from the net polarization that could develop in a uniaxially oriented, intrinsically piezoelectric material deformed in shear. See Fukada, Ferroelectrics 60, 285-96 (1984). Importantly, internal polarizations cancel each other out for other tensors of the deformation matrix. See Fukada, 1984. The sinusoidal form of d(θ) suggests a piezoelectric coefficient matrix of type $C_\infty$ or $D_\infty$ for silk fibroin (see Fukada, 1983), commonly observed for intrinsically piezoelectric biopolymers (see Fukada, 1984).

Figure 6A:
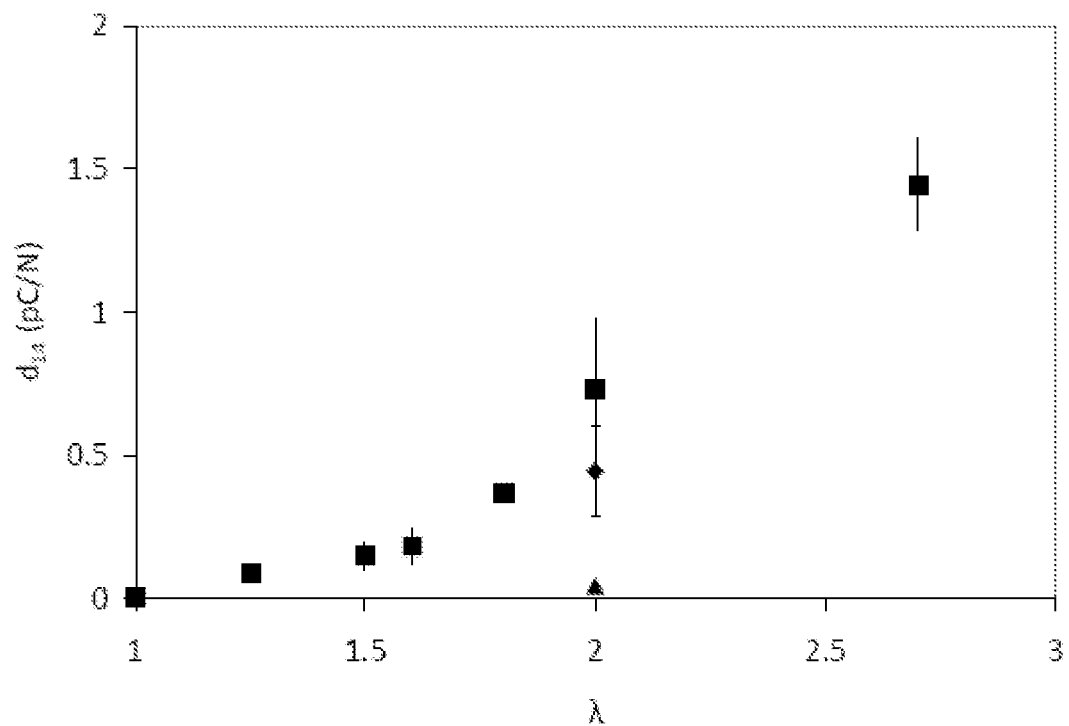
FIG. 6A is a graph showing the shear piezoelectric coefficient, $d_{14}$, of an elongated silk film, as a function of the processing parameters (zone elongated: squares; water immersion elongated: triangle; methanol treatment: diamond).

FIG. 6A shows the dependence of the room temperature shear piezoelectric coefficient ($d_{14}$) on the elongation ratio λ (for zone-elongated films), different drawing methods and methanol treatment. The absolute $d_{14}$ values increased exponentially with the elongation ratio by over two orders of magnitude, from 0.01 pC/N for λ=1 (as-dried films) to 1.5 pC/N for λ=2.7 (zone-elongated films). See, e.g., Ando et al., 1980. The measured piezoelectricity values on silk films are comparable with the absolute $d_{14}$ values reported from highly piezoelectric biopolymers (e.g. oriented collagen: 2-3 pC/N; cellulose: 0.4-0.9 pC/N), as well as oriented films of synthetic polypeptides, including polyalanine (~1 pC/N) and poly-γ-methyl-L-glutamate (PMLG) (~2 pC/N). See Fukada, Ann. NY Acad. Sci. 238, 7-25 (1974). High intrinsic shear piezoelectric coefficients were also measured from aligned films of synthetic polymers, such as poly-L-lactic acid (~10 pC/N) (see Fukada, IEEE Trns. Dielectr. Electr. Insul. 13, 1110-19 (2006)), or PMLG oriented under strong magnetic fields (~4-5 pC/N) (see Go et al., Biochimica Et Biophysica Acta 175(2), 454-56 (1969)). Stretched and electrically poled industrial polymers such as poly(vinylidene fluoride) (PVDF) reportedly exhibit tensile piezoelectric coefficients of ~30 pC/N (see Fukada, 1974). However, compared to the measurement frequency used in the majority of previous reports (10 Hz) (see, Fukada, 1983; Ando et al., 1980; Fukada, 1984; Fukada, 1974), a relatively low measurement frequency was employed herein (0.5 Hz), which may have led to an underestimation of piezoelectricity in the silk fibroin films because the leakage current may increase with decreasing the measurement frequency. Furthermore, to function as a useful biomaterial for biomedical and biotechnological applications, piezoelectric silk is advantageous compared to other piezoelectric polymers due to the all aqueous processability, biocompatibility, controllable biodegradability, and the lack of potentially immunogenic degradation byproducts.

To investigate a possible correlation between the silk II, β-sheet content ($C_β$) and the shear piezoelectric coefficient ($d_{14}$), measured values of both parameters ($P_i$) were normalized with respect to their lowest ($P_{min}$) and highest values ($P_{max}$) using $$P'_i = \frac{P_{max} - P_i}{P_{max} - P_{min}}.$$

Figure 6B:
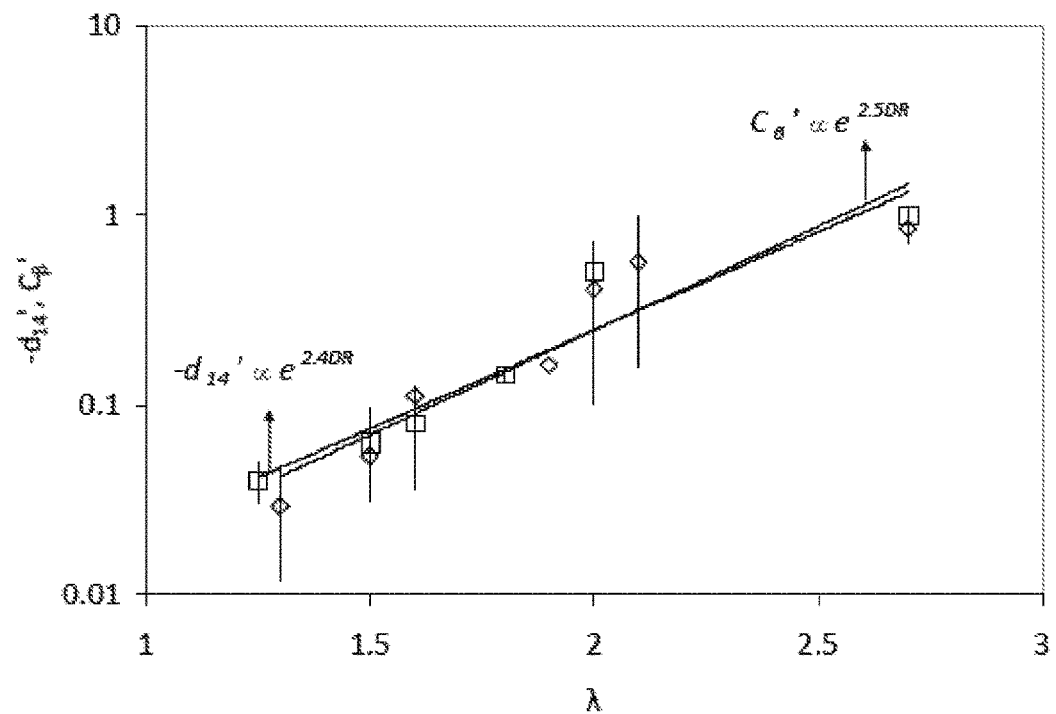
FIG. 6B is a graph showing the exponential dependence of $d_{14}'$ (squares) and $C_\beta'$ (diamonds) on the elongation ratio for zone-drawn silk films.

Both normalized parameters showed an exponential dependence on the elongation ratio with very similar exponential factors ($C_β' \propto e^{2.5\lambda}$, $-d_{14}' \propto e^{2.4\lambda}$) (FIG. 6B) for zone-elongated silk films. These results suggested a strong correlation between shear piezoelectricity and the β-sheet content.

Figure 7:
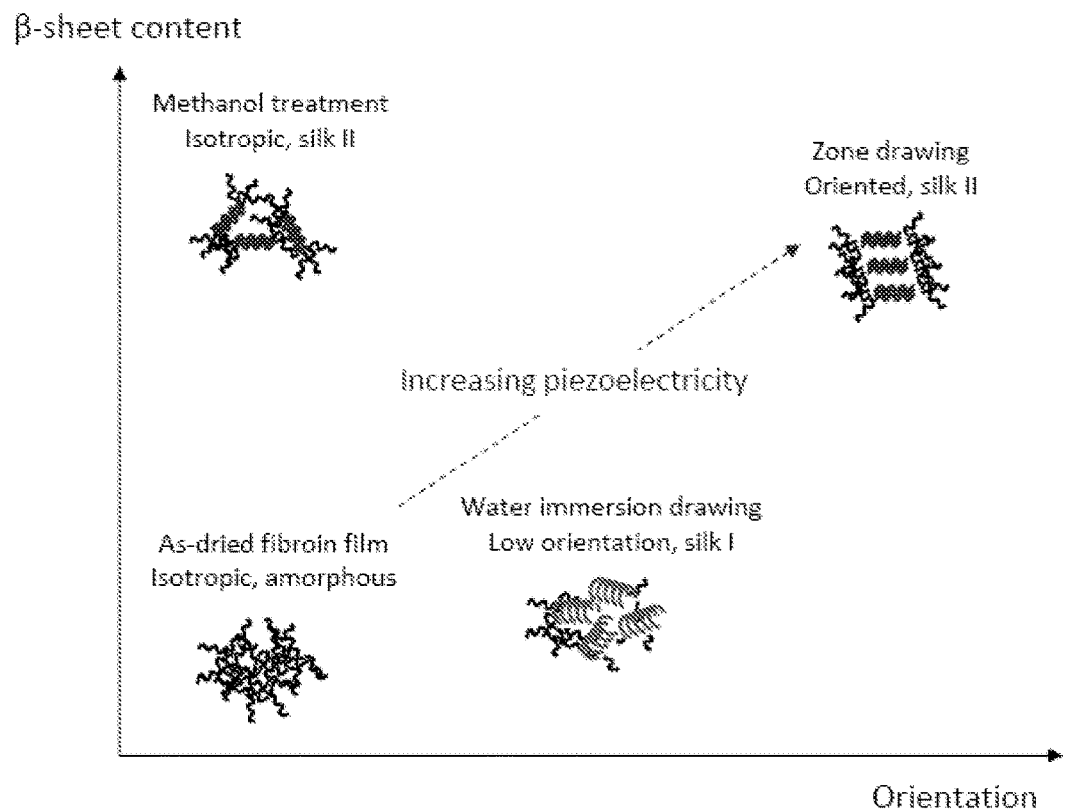
FIG. 7 is a schematic showing the correlation between the processing parameters on a silk fibroin matrix, structural characteristics of the silk fibroin matrix and the piezoelectricity in the silk fibroin matrix.

Water immersion-elongated silk films exhibited low shear piezoelectric coefficient values when compared to their zone-elongated counterparts ($d_{14}$=−0.73 pC/N for zone-elongated films and −0.046 pC/N for water immersion-elongated films, respectively) (FIG. 6A). This can be explained by the silk I structure with a low degree of orientation observed in water immersion-elongated films via FTIR and WAXD (FIG. 7). Likewise, methanol treatment of as-dried films for two days did not result in a significant improvement in silk piezoelectricity as compared with the as-dried films because of the absence of uniaxial crystal alignment, albeit the high β-sheet crystallinity induced by methanol treatment, (FIG. 7).

In sum, the correlations between the measured silk piezoelectricity and corresponding structural characterization of silk films indicate that generation or enhancement of silk piezoelectricity is due to a combination of increased β-sheet crystal content and increased crystal orientation (FIG. 7). Silk piezoelectricity may be explained by net polarization of uniaxially aligned, silk II crystals with a non-centrosymmetric, monoclinic unit cell perpendicular to the plane of the applied shear force. Shear forces, when applied in the plane of the β-sheet, may result in intra- and inter-chain slide within pleated β-sheet domains and a subsequent rotation of amide dipoles (see Fukada & Takashita, Jpn. J. Appl. Phys. 10, 722-26 (1971)), leading to an internal polarization. While an isotropic distribution of β-sheet crystal domains would lead to a cancellation of internal polarizations, uniaxial orientation of crystal domains can facilitate a net polarization (i.e., a piezoelectric effect). Methanol treatment was previously reported to increase silk piezoelectricity due to the transition of silk fibroin from random coil to β form crystallites. See Ando et al., 1980. However, the inventor has discovered that methanol treatment of zone-elongated silk films led to a slight decrease in the measured shear piezoelectricity values, although there was an increase in the apparent degree of crystallinity measured by FTIR and WAXD. The value of $d_{14}$ may be proportional to an orientation function and the average of shear piezoelectric coefficients of a single crystal in addition to the degree of crystallinity. See Fukada, 1983. The drop in silk piezoelectricity values due to methanol treatment may be attributed to the decrease in the orientation function with increasing β-sheet content.

What is claimed is:

1. A silk-based piezoelectric material comprising:
   a silk fibroin matrix characterized by uniaxially aligned silk II crystals,
   wherein the silk-based piezoelectric material is characterized in that when it is exposed to a perturbation, the material exhibits piezoelectricity having an absolute shear piezoelectricity coefficient of at least about 1.5 pC/N.

2. The silk-based piezoelectric material of claim 1, wherein the material is characterized in that it exhibits at least one of the following parameters:
   (a) oscillatory behavior between about 1 kHz and about 500 MHz;
   (b) a Mohs hardness value of about 7, a Vickers indentation hardness of about 1181 kg/mm$^2$, or a Rosival grinding hardness value of about 100;
   (c) a Young's modulus of about 100 GPa;
   (d) a Q factor between about 104 and about 107; or
   (e) a draw ratio of at least about 2.

3. The silk-based piezoelectric material of claim 1, wherein the perturbation is an applied electric field and the material is characterized in that it exhibits piezoelectricity.

4. The silk-based piezoelectric material of claim 3, wherein the piezoelectricity comprises an oscillation, vibration, pressure, force, acceleration, strain, sound, or a combination thereof.

5. The silk-based piezoelectric material of claim 1, wherein the perturbation is or comprises voltage, power, mechanical stress, strain, sound, or a combination thereof.

6. The silk-based piezoelectric material of claim 5, wherein the mechanical stress is or comprises pressure, acceleration, temperature, or force.

7. A cardiac assistance device, comprising the silk-based piezoelectric material of claim 1,
   wherein the piezoelectric material responds to a mechanical force transmitted from heart tissue, and
   wherein the response is a source of charge, voltage, and/or current.

8. The cardiac assistance device of claim 7, wherein the cardiac assistance device is a pacemaker.

9. A method of producing the silk-based piezoelectric material of claim 1, comprising steps of:
   providing a silk fibroin matrix; and
   elongating the silk fibroin matrix so as to form a silk-based piezoelectric material having an absolute shear piezoelectricity coefficient of at least about 1.5 pC/N.

10. The method of claim 9, wherein the elongating step comprises elongating the silk fibroin matrix along an axis of oscillation.

11. The method of claim 9, wherein the elongating step comprises elongating the silk fibroin matrix so as to form a silk-based piezoelectric material exhibiting one or more of the following parameters:
   a) oscillatory behavior between about 1 kHz and about 500 MHz;
   b) a Mohs hardness value of about 7, a Vickers indentation hardness of about 1181 kg/mm$^2$, or a Rosival grinding hardness value of about 100;
   c) a Young's modulus of about 100 GPa;
   d) a Q factor between about 104 and about 107;
   e) a draw ratio of at least about 2.

12. The method of claim 9, wherein elongating the silk matrix further comprises:
elongating the silk matrix at a rate of about 0.5 mm/min to about 50 mm/min.

13. The method of claim 9, further comprising:
heating at least a portion of the silk fibroin matrix to at least a glass transition temperature of the silk fibroin matrix.

14. The method of claim 9, further comprising:
contacting the silk fibroin matrix with a solvent wherein the solvent is an aqueous solvent, an organic solvent, or combination thereof.

15. A method comprising steps of:
providing the silk-based piezoelectric material of claim 1, comprising uniaxially aligned, silk II crystals;
applying perturbation to the silk-based piezoelectric material so as to produce piezoelectricity.

16. The method of claim 15, wherein the perturbation is or comprises voltage, power, mechanical stress, sound, or any combinations thereof.

17. The method of claim 15, wherein the piezoelectricity comprises oscillation of the silk-based piezoelectric material.

18. The method of claim 15, further comprising detecting the piezoelectricity.

19. The method of claim 18, wherein the piezoelectric response comprises oscillation, vibration, pressure, force, acceleration, strain, sound, or a combination thereof.

20. A device comprising a charge, voltage, and/or current source, wherein the source is or comprises the silk-based piezoelectric material of claim 1.

21. The device of claim 20, wherein the silk-based piezoelectric material comprises an agent.

22. The device of claim 21, wherein the agent is selected from a group consisting of: proteins, peptides, nucleic acids, nucleic acid analogs, nucleotides, oligonucleotides, peptide nucleic acids (PNA), aptamers, antibodies or fragments or portions thereof, antigens or epitopes, hormones, hormone antagonists, growth factors or recombinant growth factors and fragments and variants thereof, cell attachment mediators, cytokines, enzymes, drugs, dyes, amino acids, vitamins, antioxidants, antibiotics or antimicrobial compounds, anti-inflammation agents, antifungals, viruses, antivirals, toxins, prodrugs, chemotherapeutic agents, hemostatic agents, pathogens, metabolites, cells, or combinations thereof.

23. The device of claim 20, wherein the piezoelectricity exhibited by the material is energy, and the energy is harvested by the device.

24. The device of claim 23, wherein the harvested energy is stored by the device.

25. The device of claim 20, wherein the device is a sensor, an energy-capturing device, an energy-storing device, a cardiac assistance device, an actuator, or a combination thereof.

26. The device of claim 20, further comprising a capsule, wherein the device is housed in the capsule.

27. The silk-based piezoelectric material of claim 26, wherein when exposed to perturbations, the material exhibits piezoelectricity within the capsule that is detected external to the capsule.

28. The silk-based piezoelectric material of claim 27, wherein the capsule comprises contacts.

29. The silk-based piezoelectric material of claim 28, wherein the contacts are conductive so that when physically connected to the material the capsule communicates with a power source, a dynamic mechanical analyzer (DMA), an electrometer, and/or combinations thereof.

30. A method comprising steps of:
providing the device of claim 20,
implanting the device into a subject;
applying a perturbation so that piezoelectricity is produced in vivo.

31. The method of claim 30, further comprising a step of harvesting energy generated from the piezoelectricity.

32. The method of claim 31, further comprising storing the energy.

* * * * *

SEQUENCE LISTING

<160> NUMBER OF SEQ ID NOS: 22

<210> SEQ ID NO 1
<211> LENGTH: 90
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (7)..(90)
<223> OTHER INFORMATION: Wherein any of residues 7-90 may be missing.

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

```
Gly Ala Gly Ser Gly Ala Gly Ala Gly Ser
            85                  90

<210> SEQ ID NO 2
<211> LENGTH: 30
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is V, I or A.
<220> FEATURE:
<221> NAME/KEY: MISC_FEATURE
<222> LOCATION: (3)..(30)
<223> OTHER INFORMATION: Wherein any of residues 3-30 may be missing.

<400> SEQUENCE: 2

Gly Xaa Gly Xaa Gly Xaa Gly Xaa Gly Xaa Gly Xaa Gly Xaa Gly Xaa
1               5                   10                  15

Gly Xaa Gly Xaa Gly Xaa Gly Xaa Gly Xaa Gly Xaa Gly Xaa
            20                  25                  30

<210> SEQ ID NO 3
<211> LENGTH: 4
<212> TYPE: PRT
<213> ORGANISM: Bombyx mori

<400> SEQUENCE: 3

Gly Ala Ala Ser
1

<210> SEQ ID NO 4
<211> LENGTH: 15
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (14)..(15)
<223> OTHER INFORMATION: Wherein any of residues 14-15 may be missing

<400> SEQUENCE: 4

Ser Ser Ala Ala Ala Ala Ala Ala Ala Ala Ala Ala Ala Ala Ala
1               5                   10                  15

<210> SEQ ID NO 5
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(5)
<223> OTHER INFORMATION: Wherein any of residues 2-5 may be missing
<220> FEATURE:
<221> NAME/KEY: MISC_FEATURE
<222> LOCATION: (2)..(5)
<223> OTHER INFORMATION: Wherein X is any residue
<220> FEATURE:
<221> NAME/KEY: MISC_FEATURE
<222> LOCATION: (8)..(8)
<223> OTHER INFORMATION: Wherein X is any residue
```

```
<400> SEQUENCE: 5

Gly Xaa Xaa Xaa Xaa Gly Gly Xaa
1               5

<210> SEQ ID NO 6
<211> LENGTH: 4
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(4)
<223> OTHER INFORMATION: Wherein X is A, S, Y, R, D, V or W

<400> SEQUENCE: 6

Gly Gly Gly Xaa
1

<210> SEQ ID NO 7
<211> LENGTH: 12
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein residue S may be missing
<220> FEATURE:
<221> NAME/KEY: MISC_FEATURE
<222> LOCATION: (4)..(6)
<223> OTHER INFORMATION: Wherein any residues 4-6 may be missing

<400> SEQUENCE: 7

Ser Ser Ala Ala Ala Ala Ser Ser Ala Ala Ala Ala
1               5                   10

<210> SEQ ID NO 8
<211> LENGTH: 6
<212> TYPE: PRT
<213> ORGANISM: Galleria mellonella

<400> SEQUENCE: 8

Gly Leu Gly Gly Leu Gly
1               5

<210> SEQ ID NO 9
<211> LENGTH: 6
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (2)..(2)
<223> OTHER INFORMATION: Wherein X is L, I, V or P
<220> FEATURE:
<221> NAME/KEY: MISC_FEATURE
<222> LOCATION: (5)..(5)
<223> OTHER INFORMATION: Wherein X is L, I, V or P

<400> SEQUENCE: 9

Gly Xaa Gly Gly Xaa Gly
1               5

<210> SEQ ID NO 10
<211> LENGTH: 21
<212> TYPE: PRT
```

```
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(5)
<223> OTHER INFORMATION: Wherein X is Y, V, S or A
<220> FEATURE:
<221> NAME/KEY: MISC_FEATURE
<222> LOCATION: (6)..(20)
<223> OTHER INFORMATION: Wherein any of 6-20 may be missing
<220> FEATURE:
<221> NAME/KEY: MISC_FEATURE
<222> LOCATION: (10)..(10)
<223> OTHER INFORMATION: Wherein X is Y, V, S or A
<220> FEATURE:
<221> NAME/KEY: MISC_FEATURE
<222> LOCATION: (15)..(15)
<223> OTHER INFORMATION: Wherein X is Y, V, S or A
<220> FEATURE:
<221> NAME/KEY: MISC_FEATURE
<222> LOCATION: (20)..(20)
<223> OTHER INFORMATION: Wherein X is Y, V, S or A

<400> SEQUENCE: 10

Gly Pro Gly Gly Xaa Gly Pro Gly Gly Xaa Gly Pro Gly Gly Xaa Gly
1               5                   10                  15

Pro Gly Gly Xaa Tyr
            20

<210> SEQ ID NO 11
<211> LENGTH: 5
<212> TYPE: PRT
<213> ORGANISM: Argiope trifasciata

<400> SEQUENCE: 11

Gly Arg Gly Gly Ala
1               5

<210> SEQ ID NO 12
<211> LENGTH: 13
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (5)..(10)
<223> OTHER INFORMATION: Wherein any of 5-10 may be missing

<400> SEQUENCE: 12

Gly Ala Gly Ala Ala Ala Ala Ala Ala Gly Gly Ala
1               5                   10

<210> SEQ ID NO 13
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (3)..(3)
<223> OTHER INFORMATION: Wherein X is Q, Y, L, A, S or R
<220> FEATURE:
<221> NAME/KEY: MISC_FEATURE
<222> LOCATION: (5)..(5)
<223> OTHER INFORMATION: Wherein X is Q, Y, L, A, S or R
<220> FEATURE:
<221> NAME/KEY: MISC_FEATURE
<222> LOCATION: (7)..(7)
<223> OTHER INFORMATION: Wherein X is Q, Y, L, A, S or R
```

```
<220> FEATURE:
<221> NAME/KEY: MISC_FEATURE
<222> LOCATION: (8)..(8)
<223> OTHER INFORMATION: Wherein X is Q, Y, L, A, S or R

<400> SEQUENCE: 13

Gly Gly Xaa Gly Xaa Gly Xaa Xaa
1               5

<210> SEQ ID NO 14
<211> LENGTH: 16
<212> TYPE: PRT
<213> ORGANISM: Bombyx mori

<400> SEQUENCE: 14

Thr Gly Ser Ser Gly Phe Gly Pro Tyr Val Asn Gly Gly Tyr Ser Gly
1               5                   10                  15

<210> SEQ ID NO 15
<211> LENGTH: 8
<212> TYPE: PRT
<213> ORGANISM: Bombyx mandarina

<400> SEQUENCE: 15

Tyr Glu Tyr Ala Trp Ser Ser Glu
1               5

<210> SEQ ID NO 16
<211> LENGTH: 7
<212> TYPE: PRT
<213> ORGANISM: Antheraea mylitta

<400> SEQUENCE: 16

Ser Asp Phe Gly Thr Gly Ser
1               5

<210> SEQ ID NO 17
<211> LENGTH: 7
<212> TYPE: PRT
<213> ORGANISM: Antheraea yamamai

<400> SEQUENCE: 17

Arg Arg Ala Gly Tyr Asp Arg
1               5

<210> SEQ ID NO 18
<211> LENGTH: 8
<212> TYPE: PRT
<213> ORGANISM: Galleria mellonella

<400> SEQUENCE: 18

Glu Val Ile Val Ile Asp Asp Arg
1               5

<210> SEQ ID NO 19
<211> LENGTH: 18
<212> TYPE: PRT
<213> ORGANISM: Nephila madascariensis

<400> SEQUENCE: 19

Thr Thr Ile Ile Glu Asp Leu Asp Ile Thr Ile Asp Gly Ala Asp Gly
1               5                   10                  15

Pro Ile
```

```
<210> SEQ ID NO 20
<211> LENGTH: 8
<212> TYPE: PRT
<213> ORGANISM: Major ampullata

<400> SEQUENCE: 20

Thr Ile Ser Glu Glu Leu Thr Ile
1               5

<210> SEQ ID NO 21
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 21

Gly Ser Gly Ala Gly Ala
1               5

<210> SEQ ID NO 22
<211> LENGTH: 5
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (4)..(5)
<223> OTHER INFORMATION: Wherein X is any residue

<400> SEQUENCE: 22

Gly Pro Gly Xaa Xaa
1               5
```